US00RE50219E

(19) United States
(12) Reissued Patent
Tehrani

(10) Patent Number: US RE50,219 E
(45) Date of Reissued Patent: Nov. 26, 2024

(54) METHOD AND APPARATUS FOR CONTROLLING A VENTILATOR

(71) Applicant: Fleur T Tehrani, Anaheim, CA (US)

(72) Inventor: Fleur T Tehrani, Anaheim, CA (US)

(21) Appl. No.: 17/727,065

(22) Filed: Apr. 22, 2022

Related U.S. Patent Documents

Reissue of:
(64) Patent No.: 7,802,571
Issued: Sep. 28, 2010
Appl. No.: 10/935,446
Filed: Sep. 7, 2004

U.S. Applications:
(60) Provisional application No. 60/481,693, filed on Nov. 21, 2003.

(51) Int. Cl.
*A61M 16/00* (2006.01)

(52) U.S. Cl.
CPC ..... *A61M 16/026* (2017.08); *A61M 16/0051* (2013.01); *A61M 16/0063* (2014.02);
(Continued)

(58) Field of Classification Search
CPC ..... A61M 16/026; A61M 16/0051; A61M 16/0063; A61M 2202/0208;
(Continued)

(56) References Cited

U.S. PATENT DOCUMENTS 2,414,747 A 1/1947 Kirschbaum
3,734,091 A 5/1973 Taplin
(Continued)

FOREIGN PATENT DOCUMENTS

DE 4309923 A1 9/1994
EP 0 099283 A1 6/1983
(Continued)

OTHER PUBLICATIONS

L. Carmichael et al., *Diagnosis and Therapy of Acute Respiratory Distress Syndrome in Adults: An International Survey*, 11(1) Journal of Critical Care 9-18 (1996) ("Carmichael").
(Continued)

*Primary Examiner* — Karin Reichle

(57) ABSTRACT

Method and apparatus for controlling a ventilator are described. The invention can be used to control mechanical ventilators as well as respiratory assist devices such as CPAP machines. The apparatus receives input data indicative of patient's oxygen level. A controller determines PEEP, or CPAP, and $F_{IO2}$, on the basis of data indicative of the patient's oxygen level. In an alternative embodiment, the apparatus further receives input data indicative of patient's carbon dioxide levels, respiratory elastance and airway resistance, and barometric pressure. The controller further utilizes the said input data to determine the optimal values of tidal volume and breathing frequency for a next breath of the patient, and uses the respiratory elastance and airway resistance data to determine any necessary adjustments in the I:E ratio. The controller also applies safety rules, detects and corrects artifacts, and generates warning signals when needed.

42 Claims, 14 Drawing Sheets

(52) U.S. Cl.
CPC ..... *A61M 2202/0208* (2013.01); *A61M 2230/205* (2013.01); *A61M 2230/432* (2013.01); *A61M 2230/435* (2013.01)

(58) Field of Classification Search
CPC ..... A61M 2230/205; A61M 2230/432; A61M 2230/435
See application file for complete search history.

(56) References Cited

U.S. PATENT DOCUMENTS

| | | | | |
|---|---|---|---|---|
| 4,121,578 | A | 10/1978 | Torzala | |
| 4,326,513 | A | 4/1982 | Schulz | |
| 4,448,192 | A | 5/1984 | Stawitcke et al. | |
| 4,584,996 | A | 4/1986 | Blum | |
| 4,665,911 | A | 5/1987 | Williams et al. | |
| 4,773,411 | A | 9/1988 | Downs | |
| 4,889,116 | A | 12/1989 | Taube | |
| 4,986,268 | A | 1/1991 | Tehrani | |
| 5,103,814 | A | 4/1992 | Maher | |
| 5,315,990 | A | 5/1994 | Mondry | |
| 5,365,922 | A * | 11/1994 | Raemer | 128/204.23 |
| 5,388,575 | A * | 2/1995 | Taube | 128/204.23 |
| 5,402,796 | A | 4/1995 | Packer et al. | |
| 5,558,086 | A | 9/1996 | Smith et al. | |
| 5,575,283 | A | 11/1996 | Sjoestrand | |
| 5,617,846 | A | 4/1997 | Graetz et al. | |
| 5,682,877 | A | 11/1997 | Mondry | |
| 5,692,497 | A | 12/1997 | Schnitzer et al. | |
| 5,705,735 | A * | 1/1998 | Acorn | 73/23.3 |
| 5,738,090 | A | 4/1998 | Lachmann et al. | |
| 5,752,509 | A | 5/1998 | Lachmann et al. | |
| 5,937,854 | A | 8/1999 | Stenzler | |
| 6,105,575 | A | 8/2000 | Estes et al. | |
| 6,116,241 | A | 9/2000 | Huygen et al. | |
| 6,148,814 | A | 11/2000 | Clemmer et al. | |
| 6,158,432 | A | 12/2000 | Biondi et al. | |
| 6,305,374 | B1 | 10/2001 | Zdrojkowski et al. | |
| 6,355,002 | B1 | 3/2002 | Faram et al. | |
| 6,371,114 | B1 | 4/2002 | Schmidt et al. | |
| 6,390,091 | B1 | 5/2002 | Banner et al. | |
| 6,512,938 | B2 | 1/2003 | Claure et al. | |
| 6,532,958 | B1 | 3/2003 | Buan et al. | |
| 6,539,940 | B2 | 4/2003 | Zdrojkowski et al. | |
| 6,561,187 | B2 | 5/2003 | Schmidt et al. | |
| 6,578,575 | B1 | 6/2003 | Jonson | |
| 6,655,382 | B1 | 12/2003 | Kolobow | |
| 6,663,574 | B2 | 12/2003 | Faram et al. | |
| 6,668,829 | B2 | 12/2003 | Biondi et al. | |
| 6,671,529 | B2 | 12/2003 | Claure et al. | |
| 6,752,151 | B2 | 6/2004 | Hill | |
| 6,796,305 | B1 | 9/2004 | Banner et al. | |
| 7,210,478 | B2 | 5/2007 | Banner | |
| 7,802,571 | B2 | 9/2010 | Tehrani | |
| 2002/0110849 | A1 | 8/2002 | Leonhardt et al. | |
| 2003/0060725 | A1 | 3/2003 | Kline | |
| 2003/0111078 | A1 | 6/2003 | Habashi | |
| 2003/0145852 | A1 | 8/2003 | Schmidt et al. | |
| 2004/0003813 | A1 * | 1/2004 | Banner et al. | 128/204.21 |
| 2005/0051168 | A1 * | 3/2005 | DeVries et al. | 128/204.21 |
| 2007/0000494 | A1 | 1/2007 | Banner | |

FOREIGN PATENT DOCUMENTS

| | | |
|---|---|---|
| EP | 0658331 A1 | 6/1995 |
| EP | 0303502 | 12/1998 |
| GB | 835192 | 5/1960 |
| WO | 99/04841 | 2/1999 |
| WO | 99/61088 | 12/1999 |

OTHER PUBLICATIONS

The Acute Respiratory Distress Syndrome Network, *Ventilation with Lower Tidal Volumes as Compared with Traditional Tidal Volumes for Acute Lung Injury and the Acute Respiratory Distress Syndrome*, 342(18) The New England Journal of Medicine 1301-1308 (May 4, 2000) ("Ardsnet").

D.B. Waisel et al., *PEFIOS: a PEEP-FIO$_2$-SPO$_2$ Closed Loop Controller of Arterial Oxygen Saturation*, 79(3A) Anaesthesiology A287 (1993).

D.B. Waisel et al., *PEFIOS: An Expert Closed Loop Oxygenation Algorithm*, MEDINFO 95 PROC. 1132-1136 (1995).

N. R. Macintyre, *Building Consensus on the Use of Mechanical Ventilation*, 104 (2) Chest 334-335 (1993).

J. Anderson and T. East, *A Closed-Loop Controller for Mechanical Ventilation of Patients with ARDS*, 38 Biomed Sci. Instrum. 289-294 (2002) ("Anderson").

A. Rossi et al., *Intrinsic positive end-expiratory pressure* (*PEEP$_i$*), 21 Intensive Care Med., 522-536 (1995) ("Rossi").

J. Anderson et al., *Clinical Trial of a Non-Linear Closed-Loop Controller for Oxygenation During ARDS*, 22(A 188) Critical Care Medicine, Jan. 1994 (Anderson 2).

Final Written Decision, IPR2020-01199, U.S. Pat. No. 7,802,571 B2, *Hamilton Technologies LLC* v. *Fleur Tehrani*, Dec. 28, 2021 (FWD).

United States Court of Appeals for the Federal Circuit, *Fleur Tehrani* v. *Hamilton Technologies LLC*, Case# 2022-1732, Non-Precedential Opinion, Jun. 28, 2023 (the Opinion).

United States Supreme Court, Order List Regarding Petitions for Writ of Certiorari, Feb. 20, 2024, Petition Denied, Case 23-575, p. 5, *Fleur Tehrani*, Appellant v. *Hamilton Technologies LLC*, Appellee.

G. A. Saxton, Jr., and G. H. Myers, "A servomechanism for automatic regulation of pulmonary ventilation," *Journal of Applied Physiology*, vol. 11, pp. 326-328, 1957.

M. J. Frumin, N. A. Bergman, and D. A. Holaday, "Carbon dioxide and oxygen blood levels with a carbon dioxide controlled artificial respirator," *Anesthesiology*, vol. 20(3), pp. 313-321, 1959.

Y. Mitamura, T. Mikami, H. Sugawara, and C. Yoshimoto, "An optimally controlled respirator," *IEEE Transactions on Biomedical Engineering*, BME-18, pp. 330-337, 1971.

J. R. Coles, W. A. Brown, and D. G. Lampard, "Computer control of ventilation and anesthesia," *Medical and Biological Engineering*, vol. 11, pp. 262-267, 1973.

Y. Mitamura, T. Mikami, K. Yamamoto, and K. Mimura, "A dual control system for assisting respiration," *Medical and Biological Engineering*, vol. 13(6), pp. 846-854, 1975.

A. M. Hewlett, A. S. Platt, V. G. Terry, "Mandatory minute volume," *Anaesthesia*, vol. 32, pp. 163-169, 1977.

R. L. Coon, E. J. Zuperku, and J. P. Kampine, "Systemic arterial blood pH servo control of mechanical ventilation," *Anesthesiology*, vol. 49(3), pp. 201-204, 1978.

K. B. Ohlson, D. R. Westenskow, and W. S. Jordan, "A microprocessor based feedback controller for mechanical ventilation," *Annals of Biomedical Engineering*, vol. 10, pp. 35-48, 1982.

W. F. Fincham, and F. T. Tehrani, "A mathematical model of the human respiratory system," *Journal of Biomedical Engineering*, vol. 5, pp. 125-133, 1983.

F. W. Chapman, J. C. Newell, and R. J. Roy, "A feedback controller for ventilatory therapy," *Annals of Biomedical Engineering*, vol. 13, pp. 359-372, 1985.

M. H. Giard, F. O. Bertrand, D. Robert, and J. Pernier, "An algorithm for automatic control of $O_2$ and $CO_2$ in artificial ventilation," *IEEE Transactions on Biomedical Engineering*, vol. BME-32, No. 9, pp. 658-667, 1985.

T. D. East, K. P. Adriano, N. L. Pace, "Computer-controlled optimization of positive end-expiratory pressure," *Critical Care Medicine*, vol. 14, No. 9, pp. 792-797, 1986.

R. G. Ritchie, E. A. Ernst, B. L. Pate, J. P. Pearson, and L. C. Sheppard, "Closed-loop control of an anesthesia delivery system: Development and animal testing," *IEEE Transactions on Biomedical Engineering*, BME-34(6), pp. 437-443, 1987.

T. D. East, J. C. C. M. Veen, T. A. Jonker, N. L. Pace, and S. McJames, "Computer-controlled positive end-expiratory pressure titration for effective oxygenation without frequent blood gases." *Critical Care Medicine*, vol. 16(3), pp. 252-257, 1988.

(56) References Cited

OTHER PUBLICATIONS

R. Rudowski, L. Skreta, S. Baehrendtz, A. Bokliden, and G. Matell, "Lung function analysis and optimization during artificial ventilation. A personal computer-based system." *Computer Methods and Programs in Biomedicine*, vol. 31, pp. 33-42, 1990.

R. G. Ritchie, E. A. Ernst, B. L. Pate, J. P. Pearson, and L. C. Sheppard, "Automatic control of anesthetic delivery and ventilation during surgery," *Medical Progress through Technology*, vol. 16, pp. 61-67, 1990.

R. Rudowski, A. Bokliden, A. Carstensen, H. Gill, U. Ludwigs, G. Matell, "Multivariable optimization of mechanical ventilation. A linear programming approach." *International Journal of Clinical Monitoring and Computing*. vol. 8, pp. 107-115, 1991.

T. D. East, C. R. Tolle, S. McJames, R. M. Farrell, J. X. Brunner, "A non-linear closed-loop controller for oxygenation based on a clinically proven fifth dimensional quality surface," *Anesthesiology*, vol. 75, A468, 1991.

M. Dojat, L. Brochard, F. Lemaire, and A. Harf, "A knowledge-based system for assisted ventilation of patients in intensive care units," *International Journal of Clinical Monitoring and Computing*, vol. 9, pp. 239-250, 1992.

F. T. Tehrani, "Mathematical analysis and computer simulation of the respiratory system in the newborn infant," *IEEE Transactions on Biomedical Engineering*, vol. 40, No. 5, pp. 475-481, 1993.

T. P. Laubscher, W. Heinrichs, N. Weiler, G. Hartmann, and J. X. Brunner, "An adaptive lung ventilation controller," *IEEE Transactions on Biomedical Engineering*, vol. 41(1), pp. 51-59, 1994.

T. L. Fernando, J. S. Packer, and J. F. Cade, "A closed-loop system for controlling blood oxygen and carbon dioxide levels in mechanically ventilated patients," *Control Eng. Practice*, vol. 3, No. 10, pp. 1433-1440, 1995.

J. Schaublin, M. Derighetti, P. Feigenwinter, S. Petersen-Felix, and A. M. Zbinden, "Fuzzy logic control of mechanical ventilation during anesthesia," *British Journal of Anesthesiology*, vol. 77, pp. 636-641, 1996.

M. Dojat, F. Pachet, Z. Guessoum, D. Touchard, A. Harf, L. Brochard, "NeoGanesh: a working system for the automated control of assisted ventilation in ICUs," *Artificial Intelligence in Medicine*, vol. 11, pp. 97-117, 1997.

T. Fernando, J. Cade, and J. Packer, "Automatic control of arterial carbon dioxide tension in mechanically ventilated patients," *IEEE Transactions on Information Technology in Biomedicine*, vol. 6(4), pp. 269-276, 2002.

T. Lo, F. T. Tehrani, M. Rogers, M. Lum, T. Malinowski, S. Afuwape, M. Terry, B. Grundl, "A dual closed-loop controller for mechanical ventilation," (abstract), *American Journal of Respiratory and Critical Care Medicine*, vol. 165(8), supplement, part 2, Apr. 2002.

A. B. Otis, W. O. Fenn, and H. Rahn, "Mechanics of breathing in man," *Journal of Applied Physiology*, vol. 2, pp. 592-607, 1950.

I. R. Beddis, P. Collins, N. M. Levy, S. Godfrey, and M. Silverman, "New technique for servo-control of arterial oxygen tension in preterm infants," *Archives of Disease in Childhood*, vol. 54, pp. 278-280, 1979.

A. Sano, and M. Kikucki, "Adaptive control of arterial oxygen pressure of newborn infants under incubator oxygen treatments," *Proceedings of IEE*, vol. 132(Pt. D., No. 5), pp. 205-211, 1985.

C. Yu, W. G. He, J. M. So, R. Roy, H. Kaufman, and J. C. Newell, "Improvement in arterial oxygen control using multiple model adaptive control procedures," *IEEE Transactions on Biomedical Engineering*, BME-34(8), pp. 567-574, 1987.

R. E. Dugdale, R. G. Cameron, and G. T. Lealman, "Closed-loop control of the partial pressure of arterial oxygen in neonates," *Clinical Physics and Physiological Measurement*, vol. 9(4), pp. 291-305, 1988.

A. H. Morris, C. J. Wallace, T. P. Clemmer, J. F. Orme Jr., L. K. Weaver, N. C. Dean, S. Butler, M. R. Suchyta, T. D. East, D. F. Sittig, "Extracorporeal $CO_2$ removal therapy for adult respiratory distress syndrome patients: a computerized protocol controlled trial," *Râeanimation, soins intensifs, maedecine d'urgence*, vol. 6(7), pp. 485-490, 1990.

D. F. Sittig, R. M. Gardner, A. H. Morris, and C. J. Wallace, "Clinical evaluation of computer-based respiratory care algorithms," *International Journal of Clinical Monitoring and Computing*, vol. 7, pp. 177-185, 1990.

P. E. Morozoff, and R. W. Evans, "Closed loop control of $S_{aO2}$ in the neonate," *Biomedical Instrumentation and Technology*, vol. 26, pp. 117-123, 1992.

F. T. Tehrani, "A microcomputer oxygen control system for ventilatory therapy," *Annals of Biomedical Engineering*, vol. 20(5), pp. 547-558, 1992.

J. R. Anderson, T. D. East, J. Coombs, T. Clemmer, J. Orme, L. Weaver, "Clinical trial of a non-linear closed-loop controller for oxygenation during ARDS," *Critical Care Medicine*, vol. 22, A188, Jan. 1994.

F. T. Tehrani, and A. R. Bazar, "A feedback controller for supplemental oxygen treatment of newborn infants: a simulation study," *Medical Engineering and Physics*, vol. 16, pp. 329-333, 1994.

G. A. Lotti, J. X. Brunner, A. Braschi, T. Laubscher, M. C. Olivei, A. Palo, C. Galbusera, A. Comelli, "Closed-loop control of airway occlusion pressure at 0.1 second ($P_{0.1}$) applied to pressure-support ventilation: Algorithm and application in intubated patients," *Critical Care Medicine*, vol. 24(5), pp. 771-779, 1996.

D. B. Raemer, X. Ji, and G. P. Topulos, "$F_{IX}$ controller: an instrument to automatically adjust inspired oxygen fraction using feedback control from a pulse oximeter," *Journal of Clinical Monitoring*, vol. 13, pp. 91-101, 1997.

F. T. Tehrani, "A control system for oxygen therapy of premature infants," in *The Proceedings of the 23rd Annual International Conference of IEEE Engineering in Medicine and Biology Society*, vol. 23(2), pp. 2059-2062, Oct. 2001.

F. T. Tehrani, M. Rogers, T. Lo, T. Malinowski, S. Afuwape, M. Lum, B. Grundl, and M. Terry, "Closed-loop control of the inspired fraction of oxygen in mechanical ventilation," *Journal of Clinical Monitoring and Computing*, vol. 17(6), pp. 367-376, 2002.

P. Saura, L. Blanch, "How to set positive end-expiratory pressure,"0 *Respiratory Care*, vol. 47 (3), pp. 279-295, 2002.

J.M. Halter et al, "Positive End-Expiratory Pressure after a Recruitment Maneuver Prevents Both Alveolar Collapse and Recruitment/Decrectuitment," 2003, *American Journal of Respiratory and Critical Care Medicine*, 167:1620-1626.

S.E. Lapinsky et al., "Safety and efficacy of a sustained inflation for alveolar recruitment in adults with respiratory failure," 1999, *Intensive Care Medicine*, 25:1297-1301.

R.G. Brower et al., "Effects of recruitment maneuvers in patients with acute lung injury and acute respiratory distress syndrome ventilated with high positive end-expiratory pressure," 2003, *Critical Care Medicine*, 31(11):2592-2597.

* cited by examiner

METHOD AND APPARATUS FOR CONTROLLING A VENTILATOR

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application *is a reissue patent application of U.S. nonprovisional patent application Ser. No. 10/935,446, filed Sep. 7, 2004, now issued U.S. Pat. No. 7,802,571, which* claims the benefit of U.S. provisional patent application No. 60/481,693, filed Nov. 21, 2003, the entire contents of which are incorporated herein by reference. This application is related to U.S. Pat. No. 4,986,268 entitled "Method and Apparatus for Controlling an Artificial Respirator," the disclosure of which is incorporated by reference.

BACKGROUND OF INVENTION

1. Field of the Invention

The present invention relates to a method and apparatus for controlling a ventilator such as a mechanical ventilator (i.e. an artificial respirator) or a respiratory assist device. In particular, the present invention relates to a method and apparatus for controlling a ventilator based on the measured levels of oxygen of the patient on the ventilator, as well as other physical conditions of the patient.

2. Background of the Invention

Mechanical ventilators and other respiratory assist devices are extensively used to treat and manage all patient populations. In the past few decades, there have been significant changes in the features offered by the ventilators and they have become increasingly responsive to individual patient needs. However, despite much advancement in these devices, most ventilators used today are still mainly open-loop controlled devices and their added features have to some extent contributed to their complexity. The clinicians are required to make many important selections among the wide range of options available in advanced mechanical ventilators. Optimal adjustment of these machines oftentimes requires in depth knowledge about the ventilator along-with thorough review of the patient's status and his/her underlying illness. These adjustments are particularly cumbersome and frequent in more fragile and less medically stable patients.

There have been many attempts in the past to automatically control some of the main outputs of mechanical ventilators. See Y. Mitamura et al., "A dual control system for assisting respiration," Medical and Biological Engineering, vol. 13, no. 6, pages 846-854, 1975, Yu et al., "Improvement in arterial oxygen control using multiple model adaptive control procedures," IEEE Transactions on Biomedical Engineering, BME-34(8), pages 567-574, 1987, and U.S. Pat. No. 4,986,268 to F. T. Tehrani, issued Jan. 22, 1991, entitled "Method and apparatus for controlling an artificial respirator."

Also, see U.S. Pat. No. 5,103,814 to T. Maher, issued Apr. 14, 1992, entitled "Self-compensating patient respirator," Morozoff P. E., and Evans R. W., "Closed-loop control of $S_{aO2}$ in the neonate," Biomedical Instrumentation and Technology, vol. 26, pages 117-123, 1992, U.S. Pat. No. 5,365,922 to D. B. Raemer issued Nov. 22, 1994 entitled "Closed-loop non-invasive oxygen saturation control system," Tehrani et al. "Closed-loop control of the inspired fraction of oxygen in mechanical ventilation," Journal of Clinical Monitoring and Computing, vol. 17, No. 6, pages 367-376, 2002, and U.S. Pat. No. 6,671,529 to N. R. Claure et al., issued Dec. 30, 2003, entitled "System and method for closed-loop controlled inspired oxygen concentration."

Some of the prior art on this subject is focused on controlling the patient's oxygenation, and some is intended to automatically control the breathing frequency and tidal volume. The systems intended for controlling only the oxygen level of the patient on the ventilator, either do not provide the automation of all factors that affect oxygenation and/or they do not provide a reliable and sufficiently robust response against oxygen disturbances.

In addition to advancement in mechanical ventilators, there have been many attempts in recent years to prevent the collapse of the airways and apnea in spontaneously breathing patients specially during sleep, by using less elaborate machines than mechanical ventilators, generally known as CPAP machines (CPAP stands for Continuous Positive Airway Pressure). In these machines, either a constant pressure is applied to the patient's airways throughout respiration (i.e. CPAP), or a combination of CPAP and pressure support in inspiration is used to ventilate the patient (e.g. bilevel CPAP machines). See U.S. Pat. No. 4,773,411 to J. B. Downs issued Sep. 27, 1988, entitled "Method and apparatus for ventilatory therapy," International Patent Publication No. WO 99/61088 to Resmed Limited, issued Dec. 2, 1999, entitled "Ventilatory assistance for treatment of cardiac failure and Cheyne-Stokes breathing," U.S. Pat. No. 6,539,940 to R. J. Zdrojkowski et al., issued Apr. 1, 2003, entitled "Breathing gas delivery method and apparatus," and U.S. Pat. No. 6,752,151 to P. D. Hill, issued Jun. 22, 2004, entitled "Method and apparatus for providing variable positive airway pressure."

In one embodiment, the present invention describes a method and apparatus that can reliably and robustly control PEEP (or CPAP), and $F_{IO2}$. These are novel features which significantly improve the oxygenation of patients during ventilatory therapy provided by mechanical ventilators as well as respiratory devices such as CPAP machines.

Furthermore, in a more elaborate embodiment of the invention, in addition to PEEP (or CPAP) and $F_{IO2}$, the I:E ratio of the patient can be automatically adjusted and by further inclusion of the features of U.S. Pat. No. 4,986,268, the breathing frequency, and tidal volume can be automatically controlled in mechanical ventilation. Application of these features results in a significantly more effective and optimal treatment to the patient based on his/her conditions and requirements, in total or assist ventilatory therapy.

SUMMARY OF INVENTION

A method and apparatus for controlling a ventilator includes first means receiving at least input data indicative of the patient's measured oxygen levels, and in a more elaborate embodiment of the invention, the first means also receives respiratory mechanics and/or pressure-volume data, as well as data indicative of measured carbon dioxide levels of the patient. The first means which preferably comprises a programmable microprocessor, is controlled by a software algorithm to operate on the input data, and to provide digital output data to control the ventilator and the gas mixer of the ventilator. The software algorithm is divided into two control programs. One control program which can either be used by itself or along with the other program, is designed to automatically adjust $F_{IO2}$ and PEEP (or CPAP), based on at least the measured oxygen levels of the patient. The control program also operates on data from a pressure volume (PV) monitor/analyzer to set the initial PEEP value in certain groups of respiratory patients. The processing means detects hazardous conditions based on the input data and/or artifacts, replaces and/or corrects the measurement artifacts, and instructs generation of appropriate warning signals. The other control program, most of which is described in U.S. Pat. No. 4,986,268, is designed to control the frequency and ventilation for a next breath of the patient on the ventilator based on at least data indicative of measured $CO_2$ and $O_2$ levels of the patient, barometric pressure (as a reference pressure), and respiratory elastance and airway resistance (respiratory mechanics) data; and to make necessary adjustments in the I:E ratio based on the patient's respiratory mechanics data. The output data from the $1^{st}$ means indicative of PEEP (or CPAP), $F_{IO2}$, the adjustment in the I:E ratio, breathing frequency, and ventilation, and status of alarms are transmitted to a Signal Generator which is equipped with converters and/or other electronic components to generate the control and appropriate warning signals. The control signals for the breathing frequency, ventilation, PEEP (or CPAP), and the adjustment in the I:E ratio are supplied to the ventilator. The control signal for $F_{IO2}$ is supplied to a mixer regulator unit which adjusts the concentration of oxygen added to the inhalation gas in the gas mixer of the ventilator. Based on the instructions from the $1^{st}$ means, the alarm circuit generates appropriate warning signals when needed.

BRIEF DESCRIPTION OF DRAWINGS

FIGS. 1-4 illustrate a preferred embodiment of the present invention. However, it is understood that this invention is not limited to the precise arrangements shown in the figures and can be embodied in other arrangements without deviating from the scope of the invention.

FIG. 1 is a block diagram of a mechanical ventilator and the control apparatus according to an alternative embodiment of the invention.

FIG. 4 shows a preferred detailed schematic diagram of a Signal Generator and an Alarm Circuit, for use in a preferred practice of the present invention.

DETAILED DESCRIPTION

Definitions

In the specification and claims:

1—The term "ventilator" refers to a device which is used to provide total or assist ventilatory treatment to patients, and includes mechanical ventilators (i.e. artificial respirators) or CPAP (Continuous Positive Airway Pressure) machines.

2—The term "PEEP" represents "Positive End-Expiratory Pressure" and is interchangeable with the term "CPAP," which represents "Continuous Positive Airway Pressure," for example, when assist ventilation is provided to spontaneously breathing subjects.

3—The term "$F_{IO2}$" represents "concentration of oxygen in a patient's inspiratory gas" which is the same as "fraction of inspired oxygen."

4—The term I:E represents the "ratio of inspiration time to expiration time."

DESCRIPTION OF PREFERRED EMBODIMENTS

Figure 1:
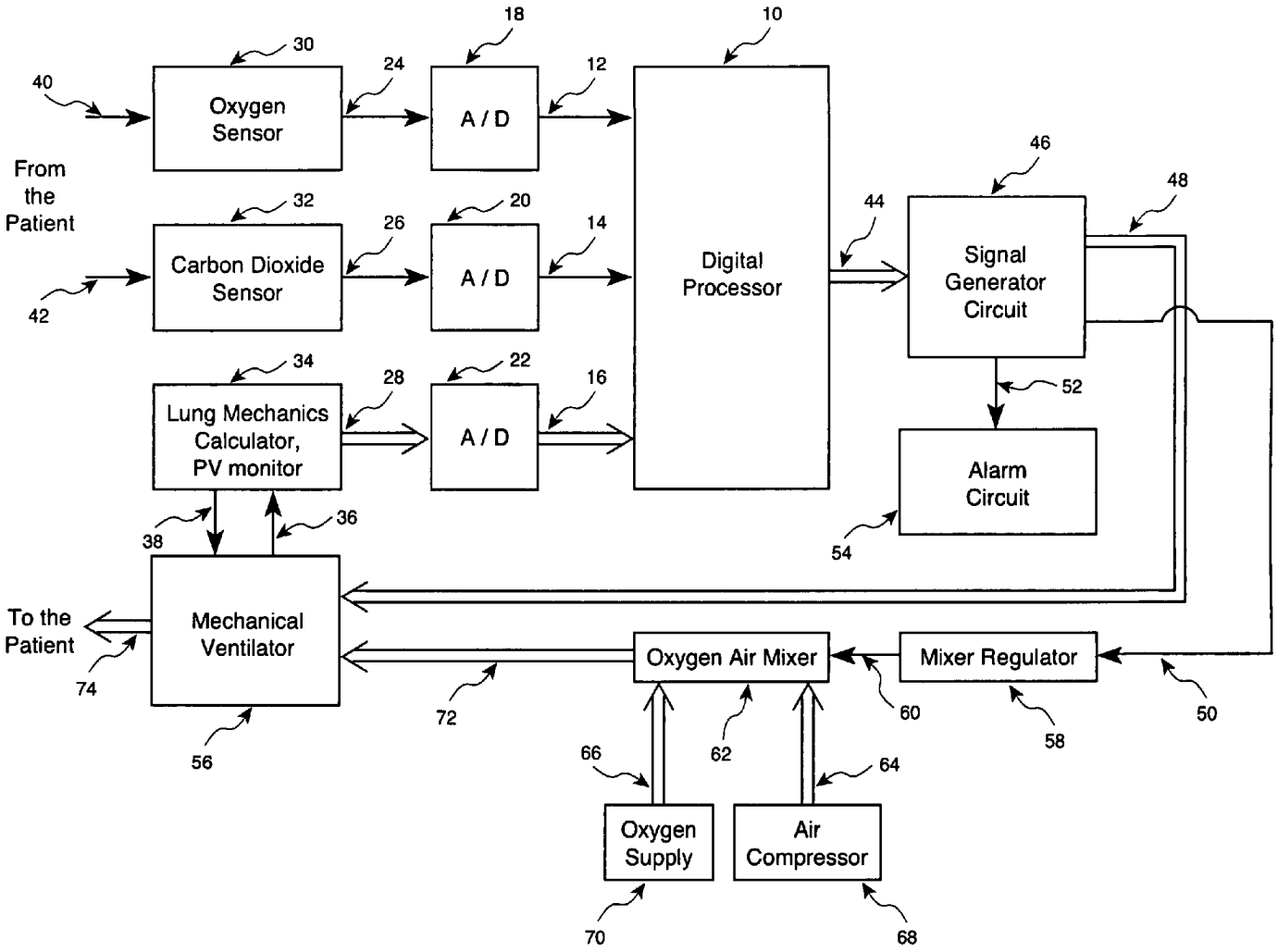

FIG. 1 shows a block diagram according to an alternative practice of the present invention. The digital processor 10 includes a programmable controller coupled to receive the outputs of 8 bit A/D converters 12, 14 and 16 as shown. The A/D converters 18 and 20 are each a single 8 bit A/D converter. The A/D converter unit 22 is an A/D board containing three 8 bit A/D converters. The inputs 24, 26, and 28 of the A/Ds are from an oxygen sensor, preferably a pulse oximeter, 30, a $CO_2$ sensor, such as a transcutaneous monitor or preferably a capnograph, 32, and a lung mechanics calculator and PV monitor, 34. The outputs 24, and 26 are each a single analog signal while the output 28 represents 3 analog signals; 1—representing respiratory elastance, 2—representing respiratory airway resistance (air viscosity factor in the lungs), and 3—representing the lower inflection point on the inspiratory or expiratory PV curve of the patient, or alternatively, the measured intrinsic PEEP (PEEPi) of the patient on the ventilator. The inputs to the oxygen sensor and the carbon dioxide sensor are respectively shown at 40 and 42 coming from the patient. The input 40 is preferably the arterial hemoglobin oxygen saturation data and the input to the $CO_2$ sensor shown at 42 is preferably the exhaled gas from the patient from which the end-tidal $CO_2$ concentration or the end-tidal partial pressure of $CO_2$ is determined by the sensor. The lung mechanics calculator and PV monitor, 34, receives data from the mechanical ventilator shown at 56, or from the patient through the ventilator circuit, on the line illustrated at 36 and communicates back to the ventilator as shown at 38. The digital processor's outputs shown at 44 are applied to a Signal Generator Circuit, illustrated at 46. The Signal Generator Circuit sends alarm instruction signals 52 to the alarm circuit 54.

The mechanical ventilator 56 receives the control signals 48 from the Signal Generator Circuit 46. These consist of signals to control PEEP, breathing frequency, tidal volume, and the adjustment in the I:E ratio of the patient. A Mixer Regulator circuit 58, receives control signals to adjust $F_{IO2}$, 50, from the Signal Generator Circuit 46. An oxygen air mixer 62 receives the adjusted output signal 60 from the Mixer Regulator 58. The concentration of oxygen in the mixer is thereby adjusted by mixing the determined concentration of oxygen 66 coming from the oxygen supply 70 and that of air 64 coming from the air compressor 68. The enriched oxygenated air 72 from the mixer is provided to the ventilator 56 which delivers it to the patient at 74.

Figure 2A:
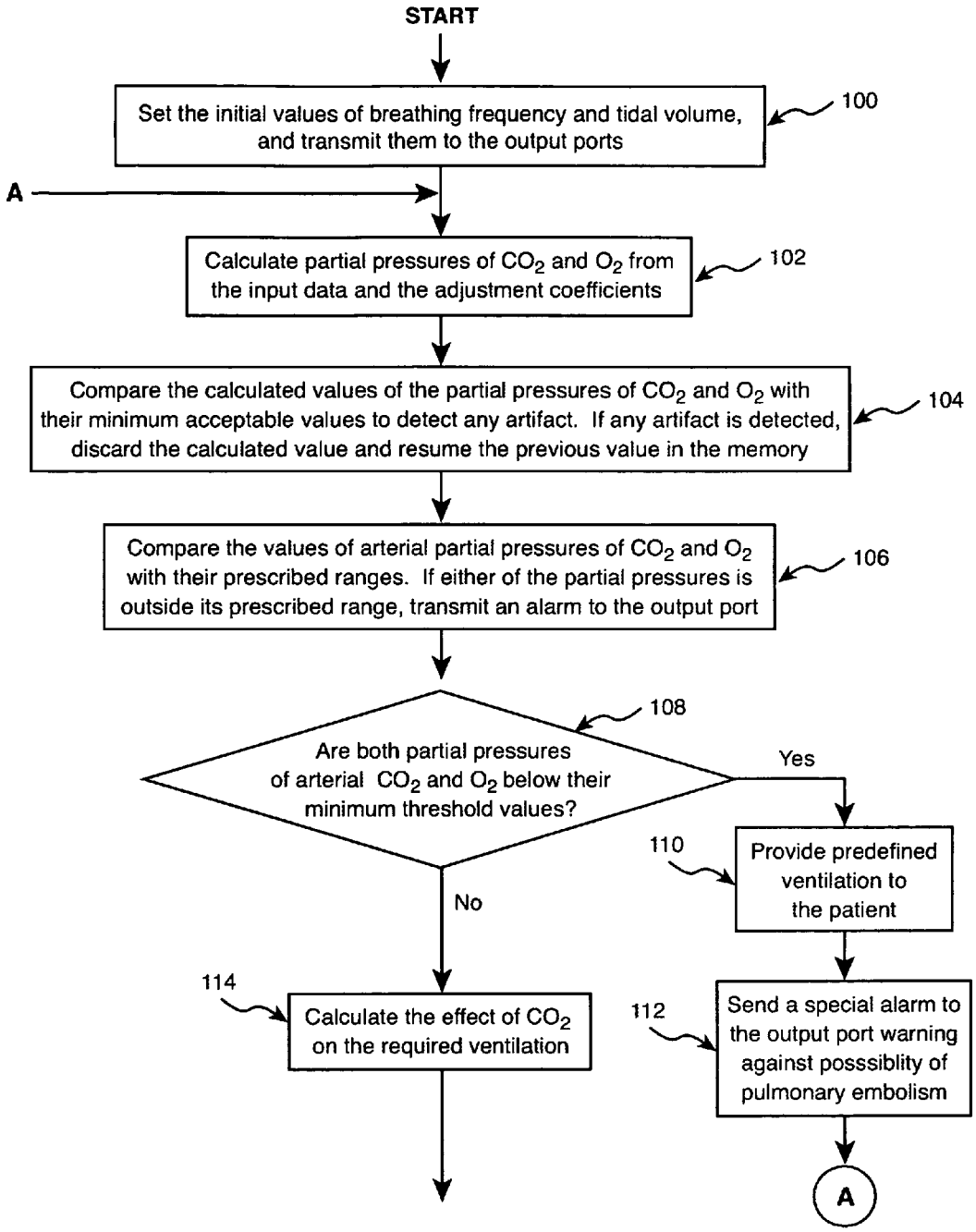
FIGS. 2a-2c show the flow chart of a software algorithm that also incorporates the control technique described in U.S. Pat. No. 4,986,268, to automatically control breathing frequency, tidal volume, and the adjustment in the I:E ratio of the patient on the ventilator, according to a preferred method of the present invention.
Figure 2B:
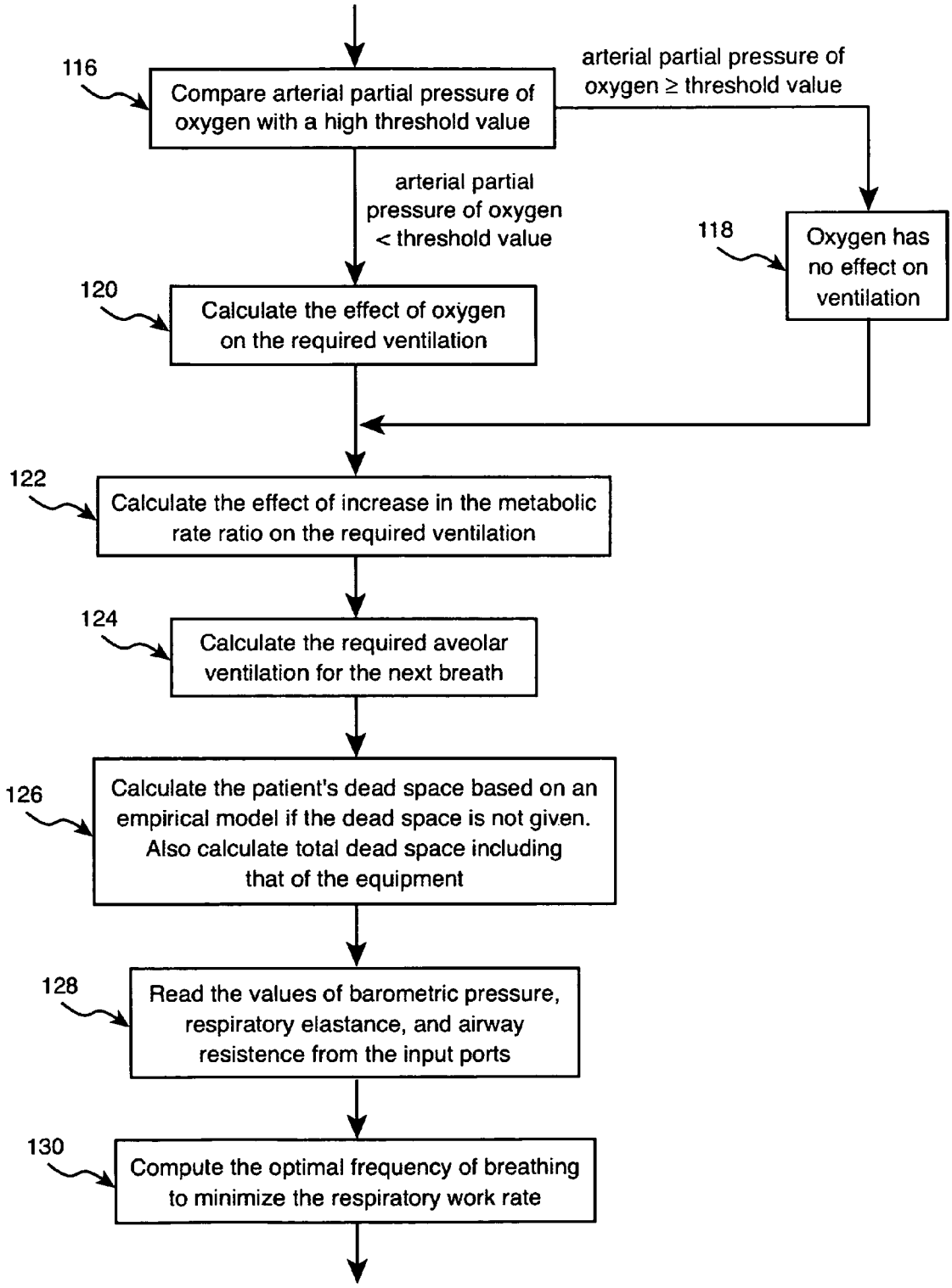
Figure 2C:
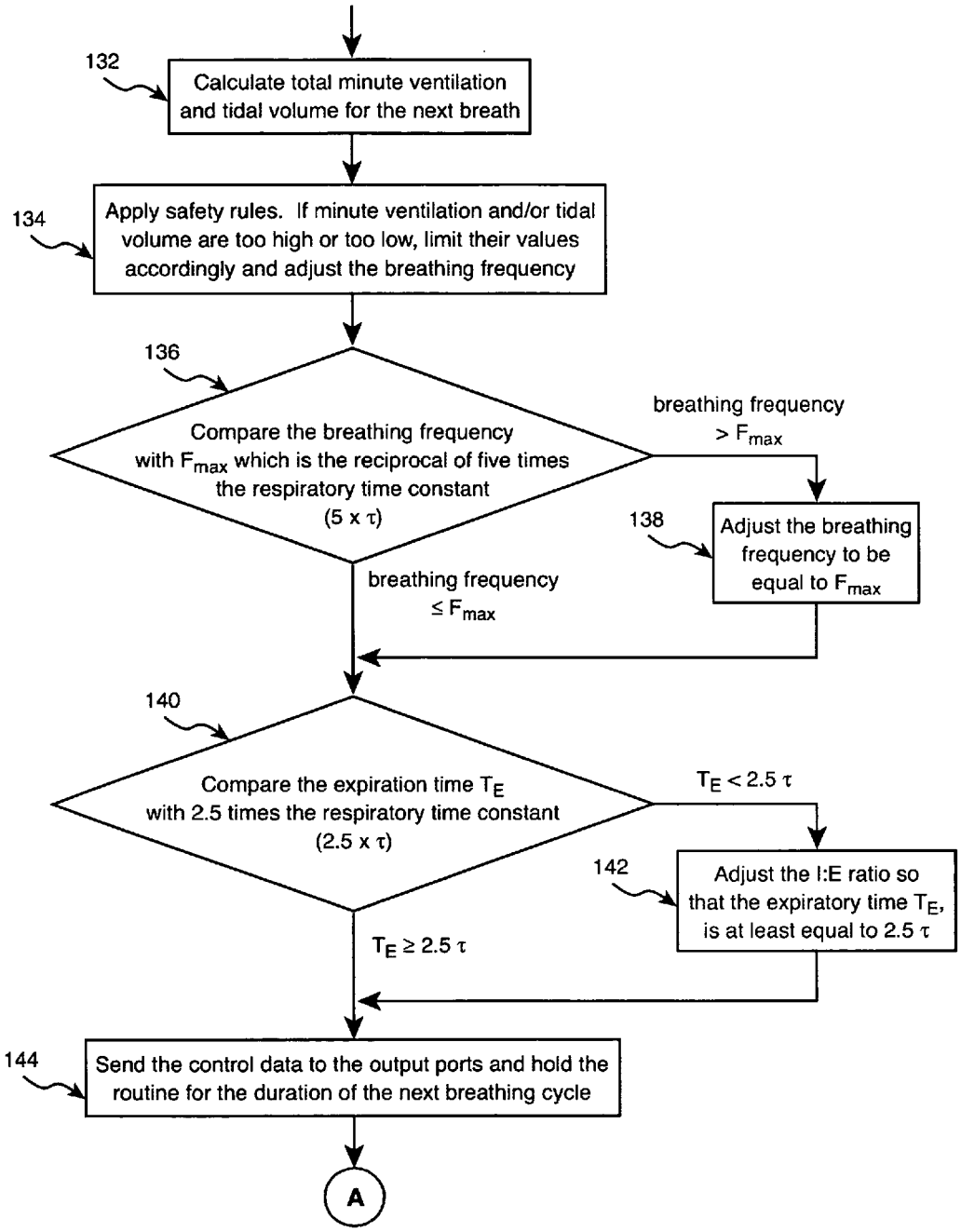
Figure 3A:
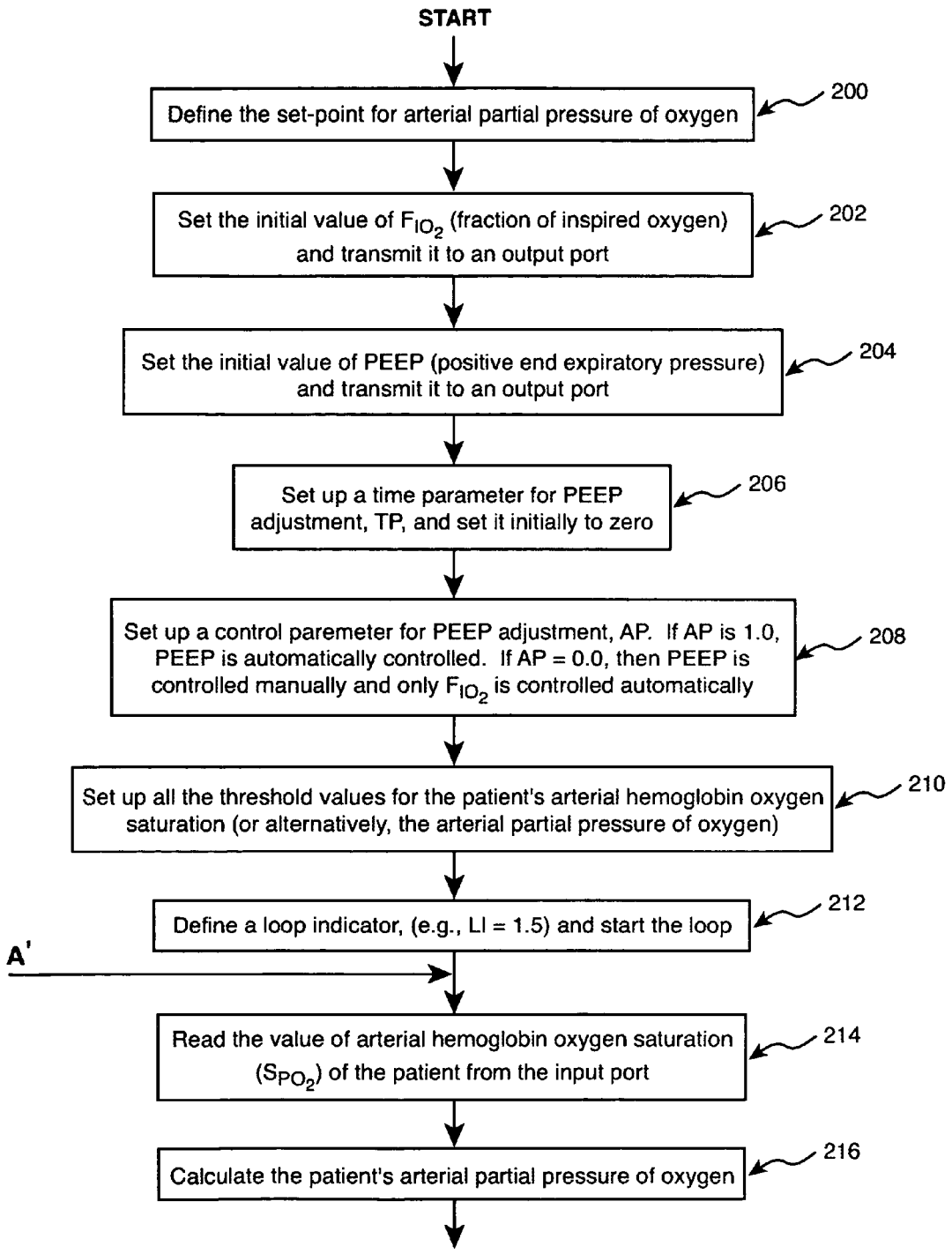
FIGS. 3a-3i show the flow chart of a software algorithm to automatically control PEEP (or CPAP) and $F_{IO2}$ according to a preferred method of the present invention.
Figure 3B:
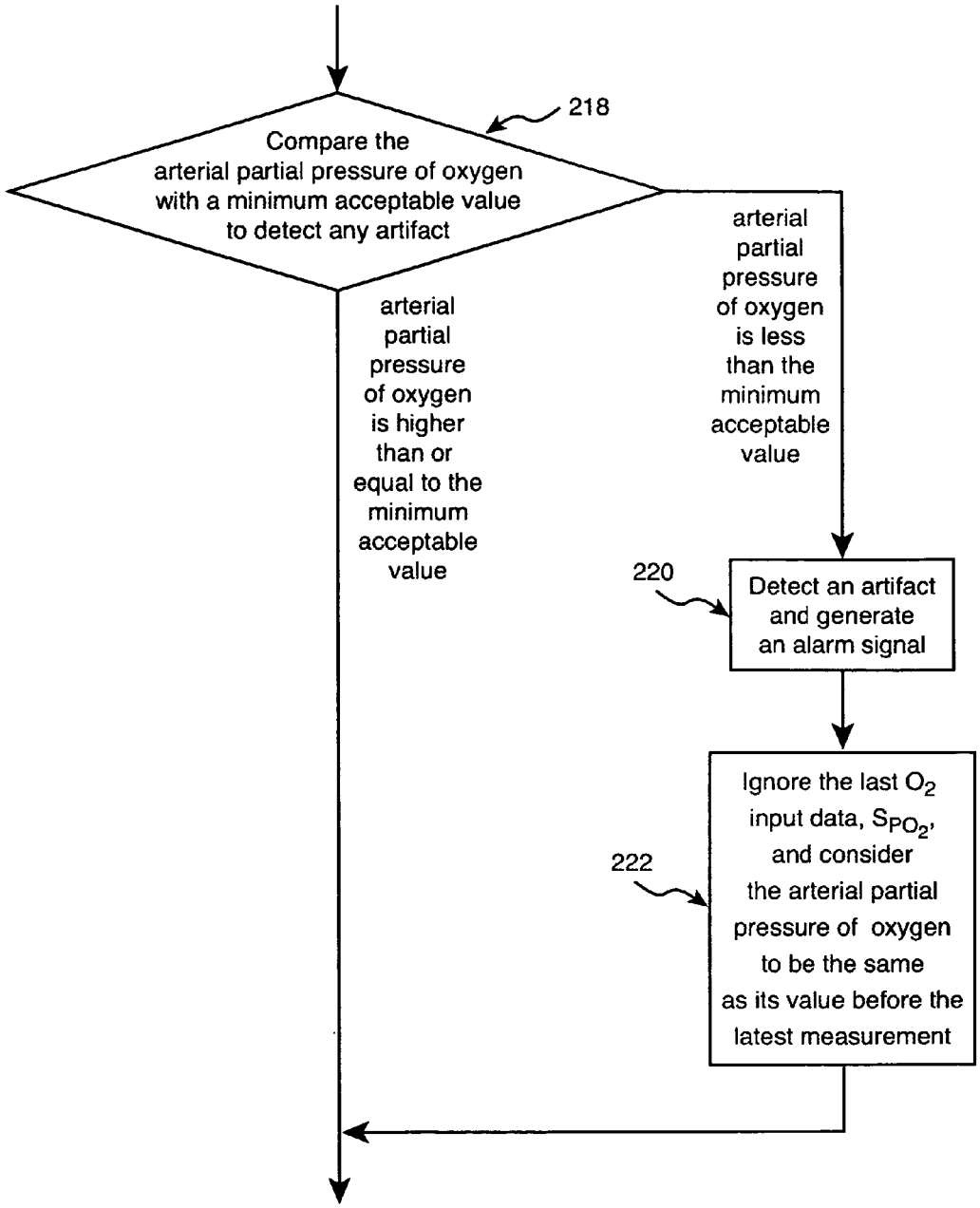
Figure 3C:
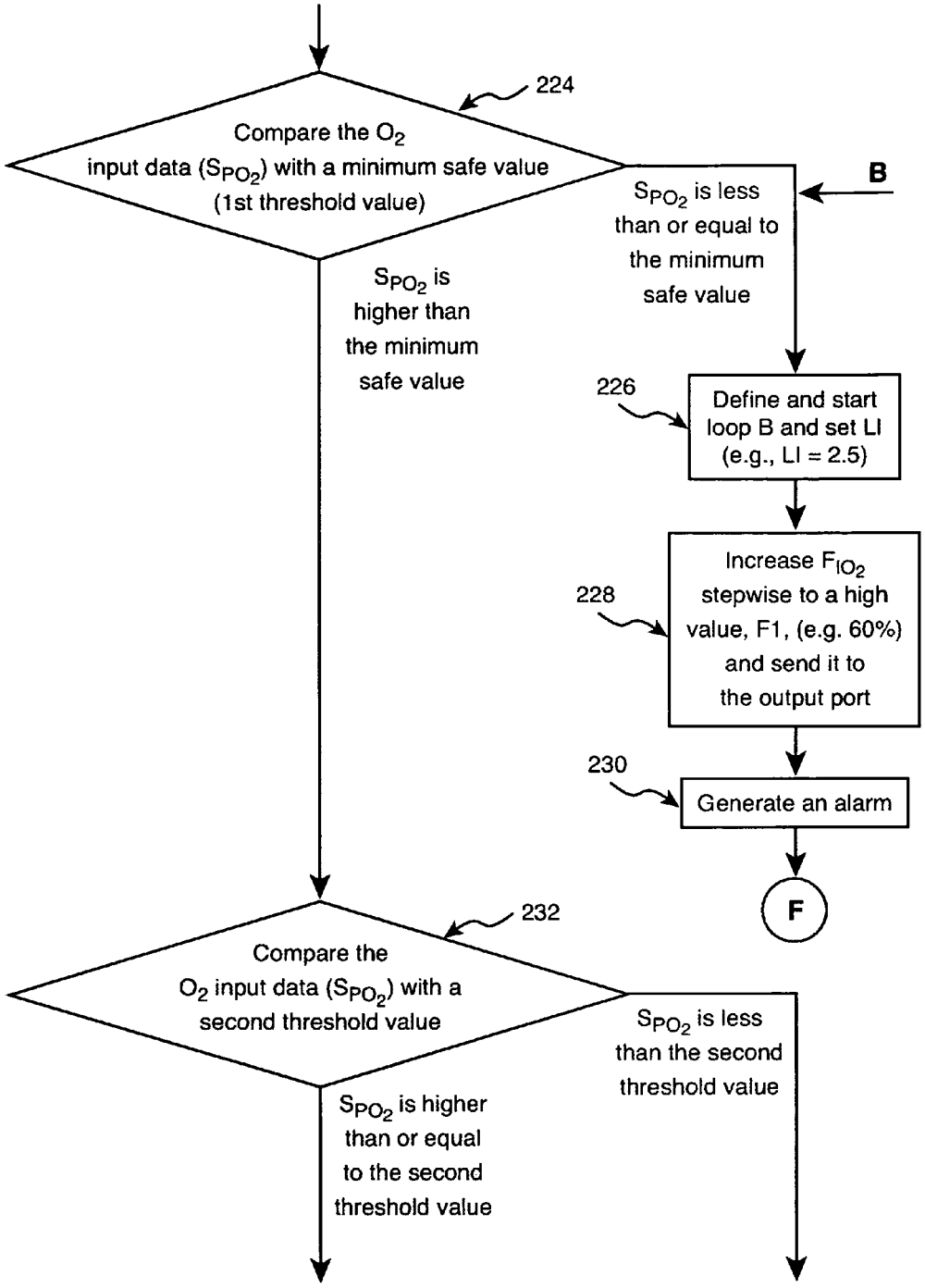
Figure 3D:
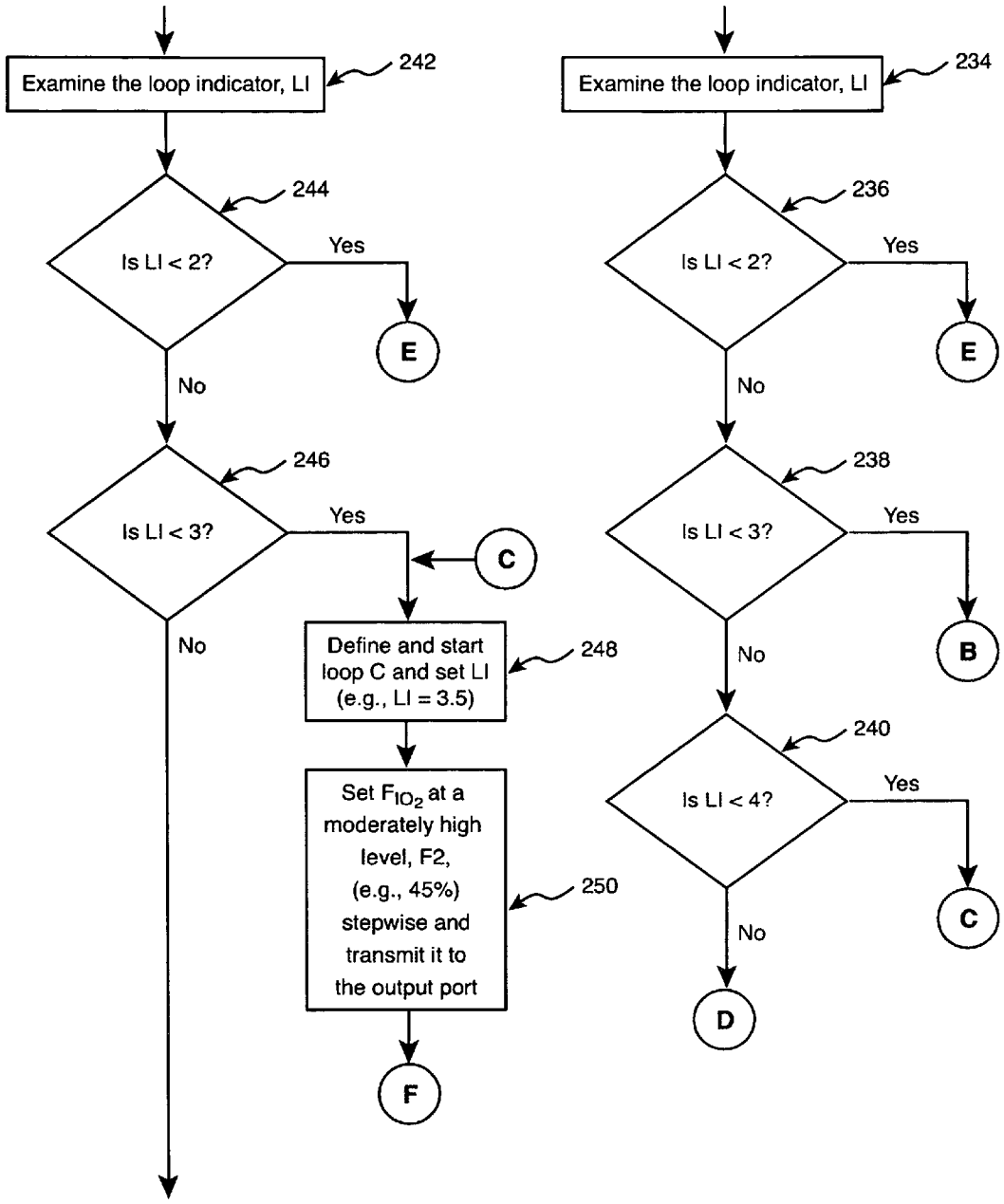
Figure 3E:
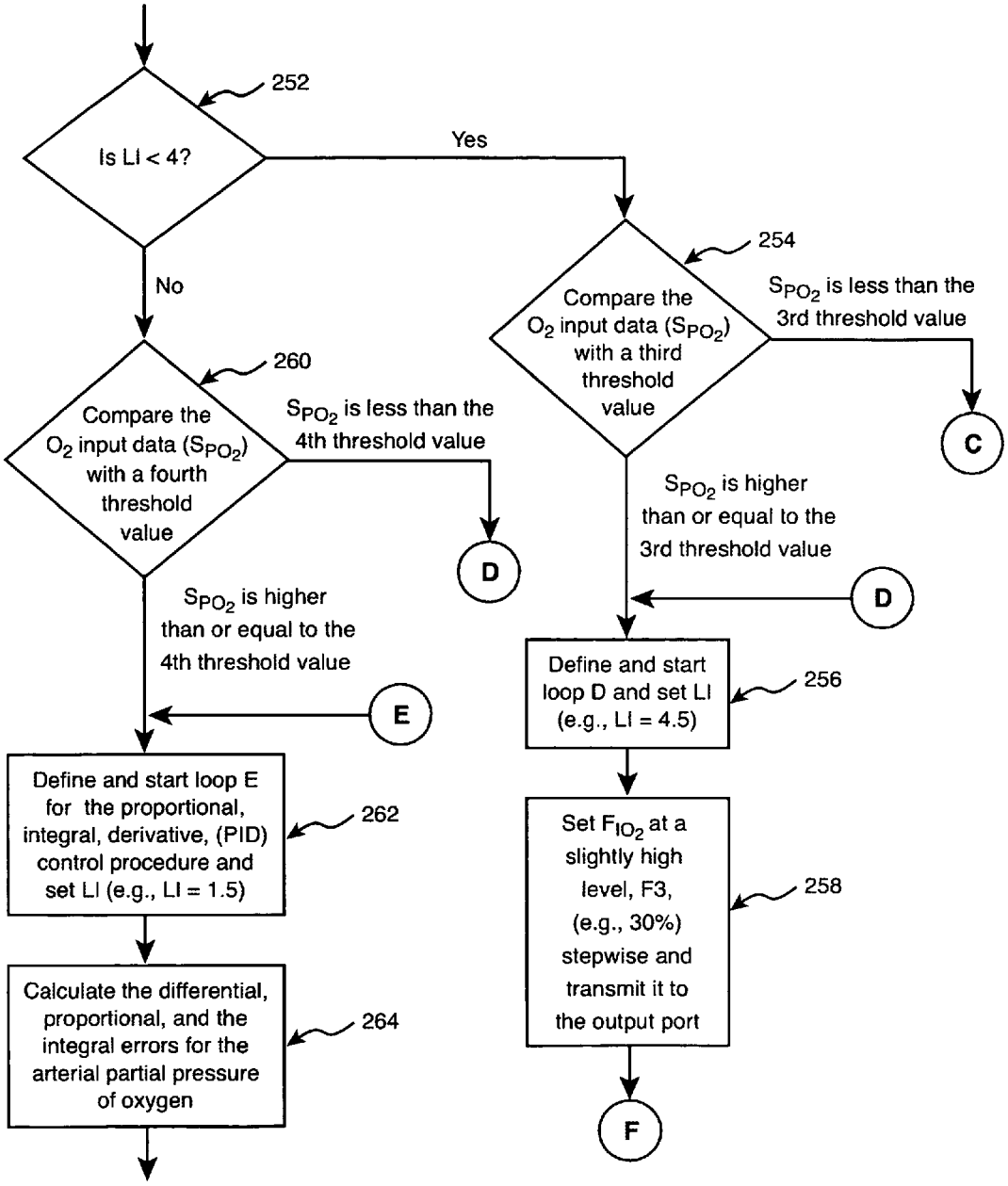
Figure 3F:
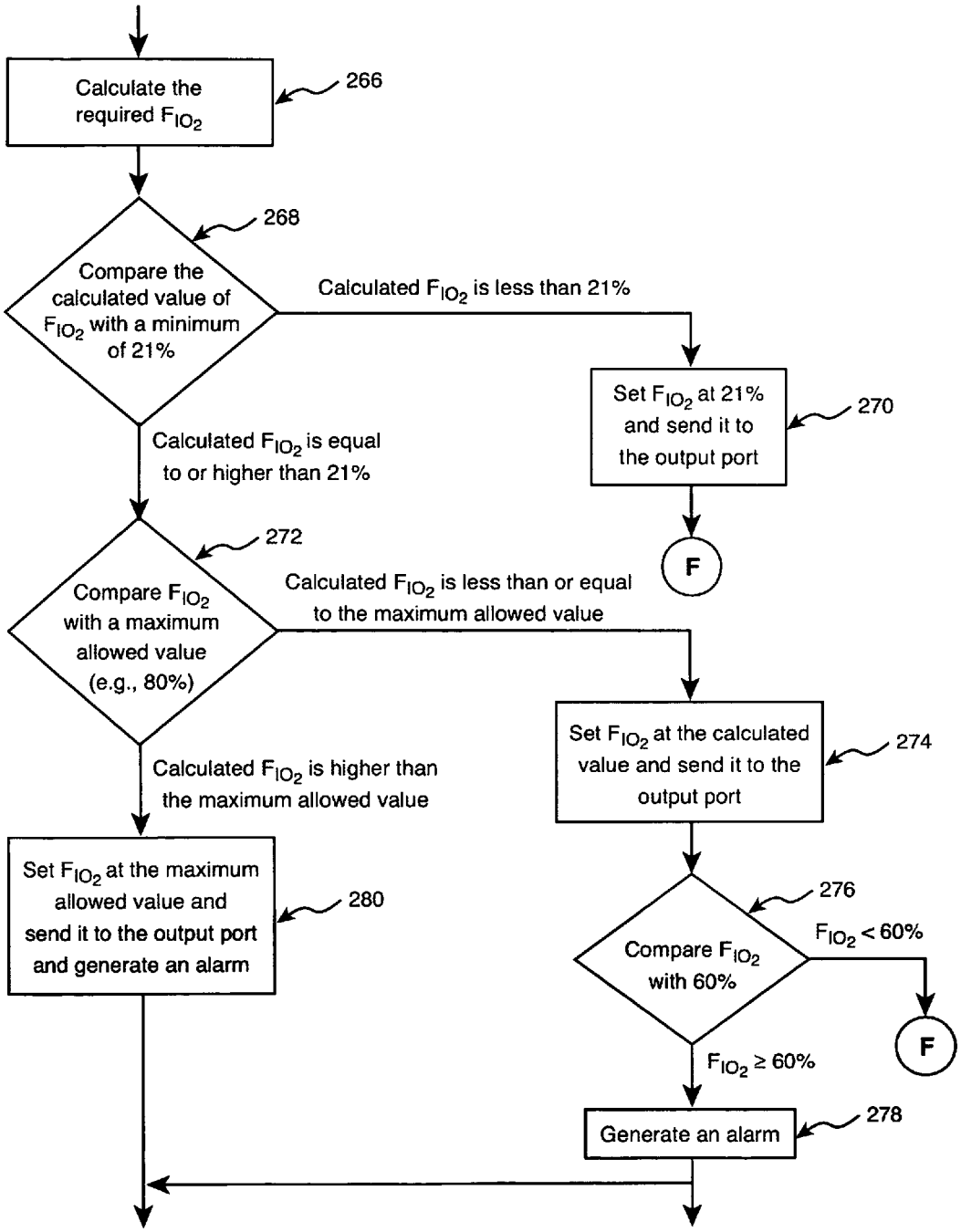
Figure 3G:
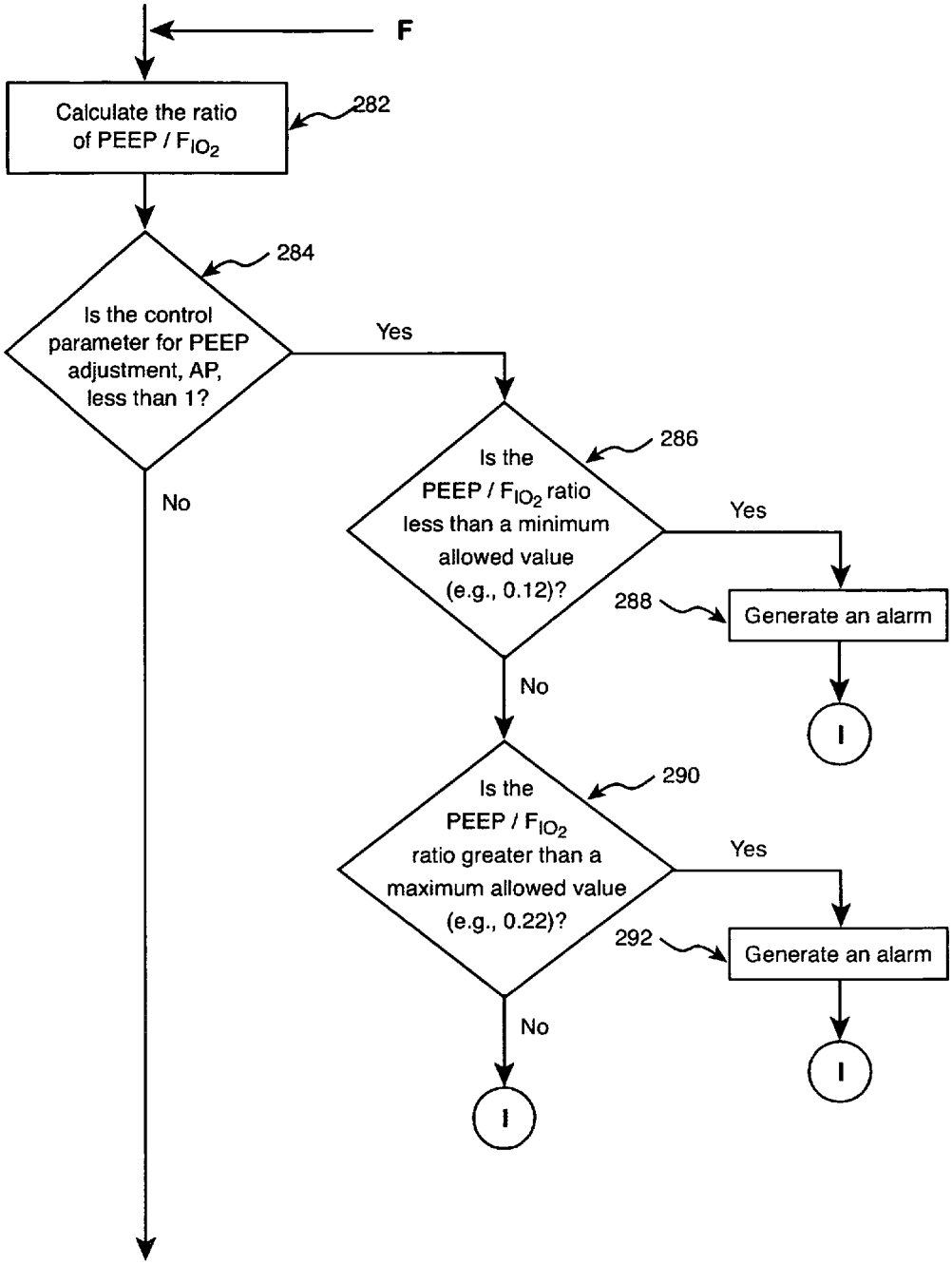
Figure 3H:
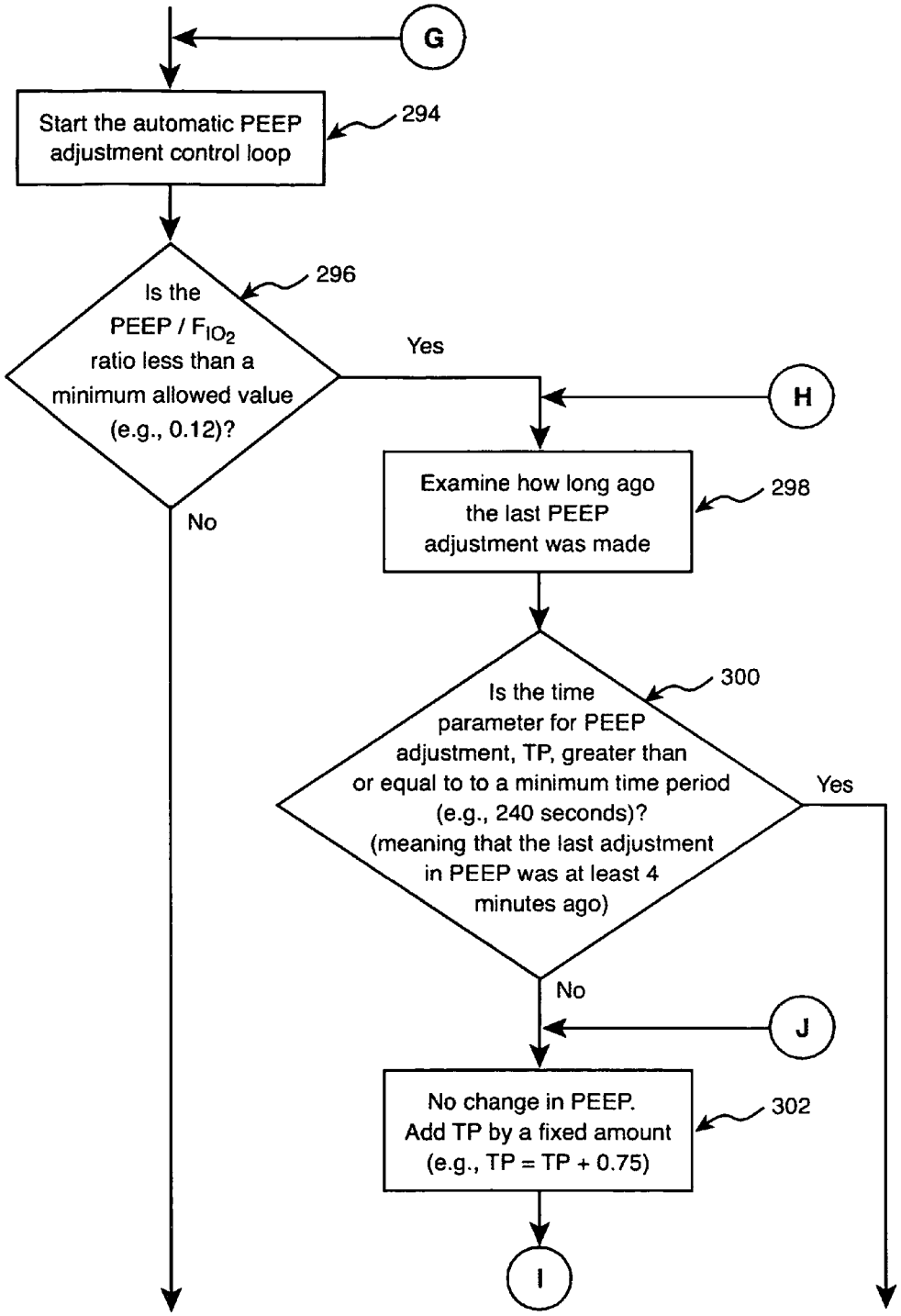
Figure 3I:
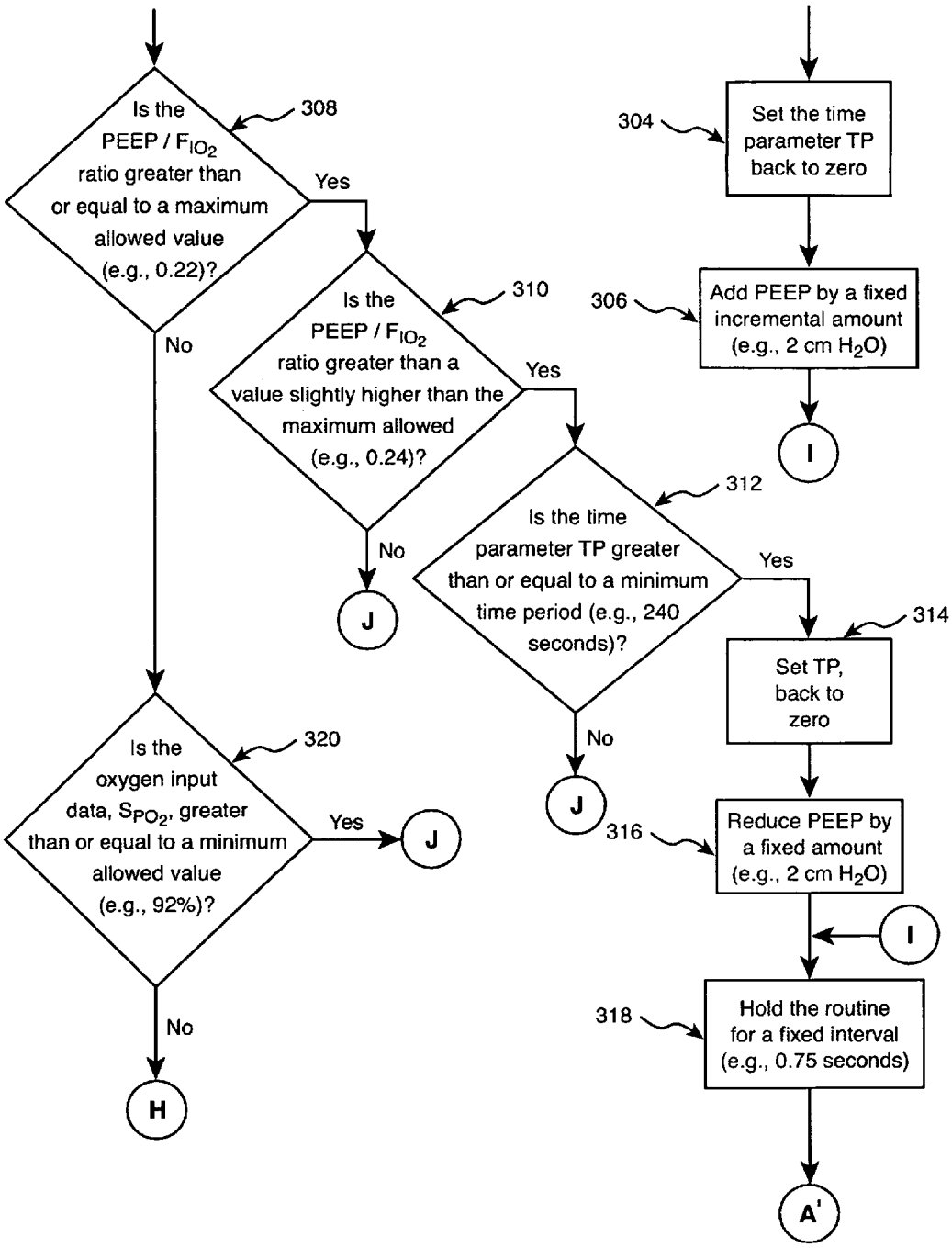

Referring to FIG. 2a-2c, there is illustrated a flow chart of the algorithm to control the breathing frequency, ventilation, and the adjustment in the I:E ratio in an alternative embodiment of the invention. As seen at the start of the flow chart, the initial values of breathing frequency and tidal volume are transmitted to the output ports in step 100. Then the main loop at A is started and in the next step at 102, based on data indicative of $CO_2$ and $O_2$ levels of the patient which are preferably provided by a capnograph and a pulse oximeter respectively, the arterial partial pressures of $CO_2$ and $O_2$ are calculated by using the following equations:

$$P_{aCO2}=P_{etCO2}+K_1$$

$$P_{aO_2}=\frac{-\ln\left[1-\left(S_{pO_2}\right)^{0.5}\right]}{0.046}+CP$$

Where $P_{aCO2}$ and $P_{aO2}$ are arterial partial pressures of $CO_2$ and $O_2$ respectively, $P_{etCO2}$ is the end-tidal partial pressure of $CO_2$ measured by the $CO_2$ sensor, and $K_1$ is the difference between the arterial partial pressure of $CO_2$ and the end-tidal partial pressure of $CO_2$. $K_1$ can be measured in advance and depending on the patient's conditions, it can be adjusted to set the desired $P_{aCO2}$ of the patient. $S_{pO2}$ is the arterial hemoglobin oxygen saturation of the patient measured by a pulse oximeter and CP is an added correction factor which is used to correct and shift $P_{aO2}$ based on the patient's measured blood pH level. If the patient's blood pH level is in the 7.45-7.55 range, CP is set to zero. Otherwise, CP needs to be adjusted by +3.5 mm Hg per every −0.1 deviation in pH from the above range. After the calculation of $P_{aCO2}$ and $P_{aO2}$, their values are compared to defined minimum acceptable levels to determine whether there has been any measurement artifact in step 104. If any artifact is detected, the calculated value is discarded and the previous calculated value is resumed. In the next step at 106, if $P_{aCO2}$ and/or $P_{aO2}$ are not within certain defined ranges, alarms are transmitted to the output ports. In the step that follows at 108, if the calculated $P_{aCO2}$ and $P_{aO2}$ values are both lower than their minimum threshold limits (which are different from the minimum acceptable values used in step 104), the possibility of pulmonary embolism is assumed, predefined levels of ventilation and breathing frequency are provided, and an alarm is generated in steps 110 and 112, and the program returns to A. However, if the calculated $P_{aCO2}$ and $P_{aO2}$ values are not found to be simultaneously lower than their minimum threshold levels in 108, then the effect of $CO_2$ on the required ventilation is calculated in step 114:

$$V_C=C_1.P_{aCO2}-C_2$$

Where $V_C$ is the ratio of alveolar ventilation as the net effect of $CO_2$ to the resting value of ventilation, $C_1$ is the sensitivity factor of the controller to $CO_2$ (e.g., $C_1$=0.405) and $C_2$ is a constant (e.g., $C_2$=14.88).

Next, in step 116, the $P_{aO2}$ value is compared to a high threshold limit of 104 mm Hg. If $P_{aO2}$ is greater than or equal to this threshold value, the effect of oxygen on ventilation is set to zero in 118, and the next step at 122 is followed. Otherwise, if $P_{aO2}$ is found to be less than the threshold value in step 116, then control is passed to step 120 in which the effect of oxygen on the required ventilation is calculated by using the following equation:

$$V_O=(4.72\times10^{-9})(104-P_{aO2})^{4.9}$$

Where $V_O$ is the ratio of alveolar ventilation as the net effect of oxygen to the resting value of ventilation. It is recognized that the above equations are based on the use of a capnograph and a pulse oximeter to measure the carbon dioxide and oxygen levels of the patient respectively. If other measurement techniques are utilized to provide data indicative of said levels, then other alternative equations may be used to determine the required ventilation for the patient, without deviating from the scope and the essential attributes of the invention.

In the next step at 122, the effect of increase in the metabolic rate ratio, MRR, (i.e. rate of metabolism/basal rate of metabolism), on ventilation is calculated by using the following equation:

$$V_M=0.988(MRR-1)$$

Where $V_M$ is the ratio of alveolar ventilation as the net effect of increase in the metabolic rate ratio, MRR, to the resting value of ventilation, and MRR is an input to the algorithm. In the next step at 124, total alveolar ventilation for the next breath is calculated:

$$V_A=(V_A \text{ at rest})(V_C+V_O+V_M)$$

Where $V_A$ is alveolar ventilation in liters/minute and $V_A$ at rest is the alveolar ventilation at rest which is input and stored in the software. In the next step at 126, the physiological dead space of the patient, and the total dead space including that of the equipment are calculated, if not provided in advance, as follows:

$$V_D=(0.1698V_A/60)+0.1587$$

$$V_{Dt}=V_D+V_{ED}$$

In these equations, $V_D$ is the patient's dead space in liters, $V_{ED}$ is the equipment dead space due to the tubes and connections, and $V_{Dt}$ is the total dead space. It should be noted that the constant factors in these equations are based on measured experimental values for adults and can therefore be different for individual patients. Also, for other patient populations, they need to be adjusted. For example the constant factor of 0.1587 should change to a much smaller value for infants (e.g., $2.28\times10^{-3}$). In the next step at 128, data indicative of barometric pressure and the patient's airway resistance (or the air viscosity factor in the lungs) and respiratory elastance are read from the input ports. The barometric pressure data which is affected mostly by the altitude, is used as a reference pressure (for the purpose of calibration) in the invention.

In the next step at 130, the optimal frequency for the next breath is computed. This calculation is based on minimization of the respiratory work rate and is done in order to stimulate natural breathing, provide a more comfortable breathing pattern to the patient, and thereby, expedite the weaning process in assisted ventilation. The following equation, which is a modified version of an equation derived in 1950 by Otis et al. to describe the control of breathing frequency in mammals, is used to calculate the optimal breathing frequency in the invention:

$$f=\frac{-K'V_D+\sqrt{(K'V_D)^2+4K'K''\Pi^2V_{AR}V_D}}{2K''\Pi^2V_D}$$

where f is the optimum breathing frequency in breaths/second, $V_{AR}$ is the alveolar ventilation in liters/second and is equal to $V_A/60$, K' is the respiratory elastance (reciprocal of respiratory compliance) in cm $H_2O$/liter and K" is the airway resistance in cm $H_2O$/liter/second. Next in step 132, the required minute ventilation and tidal volume are calculated:

$$V_E=V_A+60fV_{Dt}$$

$$V_T=V_A/60f+V_{Dt}$$

Where $V_E$ represents total minute ventilation in liters/minute and $V_T$ is tidal volume in liters. In the next step at 134, additional safety rules are applied. If breathing frequency, f, tidal volume, $V_T$, or minute ventilation are not within prescribed safe ranges, their values are limited and adjusted.

In the next step 136 which follows, the breathing frequency is compared with an upper limit value $F_{max}$. This upper limit frequency is defined as:

$$F_{max}=1/5\tau$$

Where $\tau$ is the respiratory time constant and is equal to K"/K'. If in step 136, the breathing frequency is found to be higher than $F_{max}$, then in the next step at 138, its value is reduced to $F_{max}$ (in which case $V_T$ is also adjusted according to procedures in steps 132 and 134), and step 140 is followed. Otherwise, if the computed breathing frequency is less than or equal to $F_{max}$, it does not need further adjustment and the program is transferred to step 140. In step 140, the expiration time, $T_E$, is compared to 2.5 times $\tau$. If it is found to be less than 2.5 $\tau$, then step 142 is followed and the I:E ratio (the ratio of the inspiratory time to the expiratory time) is adjusted, so that $T_E$ becomes at least equal to 2.5 $\tau$. Otherwise, if $T_E$ is found to be greater than or equal to 2.5 $\tau$ in step 140, it does not need to be adjusted (i.e. the adjustment value is zero) and the program is transferred to step 144. The reason for the adjustments in the breathing frequency and $T_E$ in steps 138 and 142 mentioned above, is to provide sufficient time for exhalation based on the patient's respiratory time constant and to avoid build up of intrinsic positive end-expiratory pressure (PEEPi).

In step 144 that follows, the calculated values for ventilation, breathing frequency, and the adjustment in the I:E ratio for the next breath are provided to the output ports. At this point, if the ventilator is in the pressure control/assist mode, the inspiratory pressure is calculated by using the following equation:

$$P_m=K'V_T+PEEP$$

where $P_m$ is the inspiratory pressure in cm $H_2O$. Thereafter, the control data indicative of $P_m$ is also provided to an output port and the routine is held for the duration of the next breathing cycle. After the delay is passed, the program returns to the beginning of the loop at A.

It should be noted that the major portion of the procedure depicted in FIG. 2 to calculate the optimal breathing frequency and tidal volume of the breaths of a patient and controlling them automatically, has been described in U.S. Pat. No. 4,986,268. In the present invention, the necessary adjustments in the I:E ratio are controlled automatically as described above, and the levels of $F_{IO2}$ and PEEP are automatically controlled by another algorithm which is described next.

Referring to FIGS. 3a-3i, there is illustrated a flow chart of a control algorithm which is operated upon by the digital processor. This algorithm is either run by itself, or in an alternative embodiment of the invention, it is run in parallel to the algorithm of FIGS. 2a-2c described above. The purpose of this algorithm is to automatically control the levels of $F_{IO2}$ and PEEP provided to the patient on the ventilator and thereby improve the patient's oxygenation. The method depicted in FIGS. 3a-3i can be used for patients on mechanical ventilation or those on respiratory assist devices receiving CPAP treatment. Depending on the type of the ventilatory treatment, the term PEEP in the flow chart is meant to be interchangeable with CPAP.

As is seen, at the start of the flow chart, the desired set point for arterial partial pressure of oxygen of the patient is defined in step 200. This is done on the basis of the patient's conditions and his/her underlying illness. Then in the next step at 202, the initial value of $F_{IO2}$ is set and transmitted to the output port.

In step 204 that follows next, the initial value of PEEP is set and transmitted to an output port. The initial value of PEEP can be set by using different options. For certain patient groups such as COPD patients, the initial PEEP can be chosen to be 80% to 85% of the intrinsic PEEP (PEEPi) which needs to be measured in advance. For some other patient groups such as ARDS patients, the initial PEEP setting can be chosen to be 3-4 cm $H_2O$ above the lower inflection pressure point of the inspiratory (or the expiratory) pressure volume curve of the patient. This value can either be calculated by the lung mechanics calculator and PV monitor unit and provided automatically to the digital processor via an input port, or the calculated value of the pressure can be provided manually by the clinician either through one of the input ports or via software. The third option is that the clinician arbitrarily decides an initial setting for PEEP and provides it to the digital processor, preferably via software. After setting the initial PEEP value in 204, the next step in 206 is followed. At this point, a time parameter (e.g., TP) for PEEP adjustment is defined and initially set to zero. The purpose of defining this parameter is to guarantee that PEEP adjustments are done only after a certain time has elapsed since the latest adjustment, thereby giving enough time to an adjustment in PEEP to make an impact on the patient's oxygenation.

In step 208 which follows next, another parameter, AP, for PEEP adjustment is defined. If this parameter is set to zero, then PEEP is controlled manually and only $F_{IO2}$ is automatically adjusted. If AP is set to one, then both $F_{IO2}$ and PEEP are automatically controlled.

In the next step 210, the threshold values for arterial hemoglobin oxygen saturation, $S_{pO2}$, (or alternatively for arterial partial pressure of oxygen) are defined. In a preferred practice of the invention, four threshold values are defined for $S_{pO2}$ and they are set at 90%, 93%, 95%, and 97% respectively. However, the threshold values may differ for different patients. They should be defined based on the patient's conditions and the desired levels of oxygenation.

Next, program control passes to step 212 in which a loop indicator (e.g., LI) is defined and is set to 1.5, and the main loop starts at A'.

In the next step in 214, the patient's $S_{pO2}$ data is read from one of the input ports, and in step 216, the arterial partial pressure of oxygen is calculated from the $S_{pO2}$ data as:

$$P_{aO_2} = \frac{-\ln\left[1-\left(S_{pO_2}\right)^{0.5}\right]}{0.046} + CP$$

Where $P_{aO2}$ is the arterial partial pressure of oxygen, and CP is an added correction factor which is used to shift $P_{aO2}$ based on the patient's measured blood pH level. If the patient's blood pH is within 7.45-7.55, then CP is set to zero. Otherwise, for every +0.1 deviation in pH from this range, CP is adjusted by −3.5 mm Hg as was also mentioned in the description of FIG. 2 earlier.

In step 218 that follows next, the calculated partial pressure of oxygen, $P_{aO2}$, is compared with a minimum acceptable value. This is done to detect artifacts in the measurement of $S_{pO2}$. If the calculated $P_{aO2}$ is found to be less than the minimum acceptable value, then control passes to step 220 in which an artifact is assumed and an alarm is generated. Then step 222 is performed in which the $S_{pO2}$ data is discarded and the previous value Of $P_{aO2}$ in the memory is resumed and step 224 is followed. However, if in 218, the calculated $P_{aO2}$ is found to be greater than or equal to the minimum acceptable value, its value is accepted and control passes to step 224.

In step 224, $S_{pO2}$ is compared to a minimum safe value, which is the first threshold value defined previously in step 210 (e.g., 90%). If $S_{pO2}$ is less than or equal to the minimum safe value, loop B is started in 226 and the loop indicator, LI, is set to 2.5. Then in step 228, $F_{IO2}$ is increased stepwise (i.e. in a step-like arrangement) to a high value, F1, (e.g., 60%), and an alarm is generated in 230. Control then passes to loop F at which the procedure of PEEP adjustment begins as will be described later. However, if $S_{pO2}$ is found to be higher than the minimum safe value in step 224, control passes to 232 where $S_{pO2}$ is compared to a second threshold value (e.g., 93%). If $S_{pO2}$ is less than the second threshold value, then steps 234 and 236 are followed in which the loop indicator, LI, is examined and compared to 2. If LI is less than 2, control passes to another loop E which will be described later. If LI is greater than or equal to 2, the next step in 238 is performed in which LI is compared to 3. If LI is less than 3, control passes to loop B (where $F_{IO2}$ was set high at F1, e.g., 60%), otherwise, the program transfers to step 240. In this step, LI is compared to 4. If it is less than 4, control passes to loop C; otherwise, the program transfers to loop D (loops C and D will be described later).

Back to step 232, if $S_{pO2}$ is found to be higher than or equal to the $2^{nd}$ threshold value (e.g., 93%), then steps 242 and 244 are followed in which LI is compared to 2. If it is less than 2, control passes to loop E. Otherwise, in the next step at 246, LI is compared to 3. If less than 3, loop C is defined and started at 248, and LI is set to 3.5. Then in step 250, $F_{IO2}$ is set stepwise at a moderately high value, F2 (e.g., 45%), and control transfers to loop F in which the procedure of PEEP adjustment is followed. However, if in step 246, LI is found to be greater than or equal to 3, control passes to step 252 in which LI is compared to 4. If LI is less than 4, then $S_{pO2}$ is compared to a third threshold value (e.g., 95%) in step 254. If $S_{pO2}$ is less than the third threshold value, control passes to loop C in which $F_{IO2}$ was set at a moderately high level, F2 (e.g., 45%). Otherwise, if $S_{pO2}$ is found to be higher than or equal to the third threshold value in 254, then the next step in 256 is followed in which loop D is defined and started and LI is set to 4.5. Next in step 258, $F_{IO2}$ is set stepwise at a slightly high level, F3 (e.g., 30%), and control passes to loop F.

Back to step 252, if LI is found to be greater than or equal to 4, then $S_{pO2}$ is compared to a $4^{th}$ threshold value (e.g., 97%) in step 260. If $S_{pO2}$ is less than the $4^{th}$ threshold value, control passes to loop D in which $F_{IO2}$ was set at a slightly high value, F3 (e.g., 30%). Otherwise, if $S_{pO2}$ is higher than or equal to the $4^{th}$ threshold value in 260, then loop E is started in 262 and LI is set to 1.5. In loop E, a proportional, integral, derivative (PID) control procedure is performed to adjust $F_{IO2}$ (PID control is a control technique comprising proportional, integral, and derivative terms). In the next step at 264, using the $P_{aO2}$ set point defined in step 200, the proportional, differential, and integral components of error are calculated as follows:

$$Y_1(k)=P_{aO2}(\text{set-point})-P_{aO2}$$

$$Y_2(k)=[Y_1(k)-Y_1(k-1)]/T$$

$$Y_3(k)=Y_3(k-1)+TY_1(k)$$

In the above equations, $Y_1(k)$, $Y_2(k)$, and $Y_3(k)$ represent the proportional, differential, and integral components of error in $P_{aO2}$ respectively, and T is a sampling interval.

In step 266 that follows, the required $F_{IO2}$ is calculated by using the following equations:

$$E(k)=\alpha Y_1(k)+\beta Y_3(k)+\gamma Y_2(k)$$

$$G(k)=E(k)+0.21$$

Where E(k) is an error function, α, β, and γ are the PID coefficients, and G(k) is the required $F_{IO2}$. In a preferred practice of the invention, T is set to 0.75 seconds, and α, β, and γ are set to $6.45\times10^{-5}$, $3.22\times10^{-5}$, and $7.29\times10^{-6}$ respectively. These parameters were tuned to minimize steady-state oscillations and to keep the overshoot/undershoot in the $F_{IO2}$ response of the PID controller below 25% of the total change. It is also recognized that other error correction schemes can be used to determine $F_{IO2}$. As long as those schemes reduce the error in the oxygen level of the patient in a similar way as described above, they will be within the scope of the present invention.

In the next step in 268, the calculated value of $F_{IO2}$ is compared with a minimum of 0.21 (i.e. 21%). If the $F_{IO2}$ value is less than 21%, in step 270 which follows, it is set to a minimum of 21% and control passes to loop F. However, if in 268, $F_{IO2}$ is found to be greater than or equal to 21%, control passes to step 272 in which $F_{IO2}$ is compared to a maximum allowed value (e.g., 80%). If $F_{IO2}$ is less than or equal to the maximum allowed value, the next step in 274 is followed where the calculated value of $F_{IO2}$ is sent to the output port and control passes to step 276. In this step $F_{IO2}$ is compared to 60%. If it is less than 60%, control passes to loop F. Otherwise, an alarm is generated in 278 and then control transfers to loop F.

Back to step 272, if the calculated value of $F_{IO2}$ is found to be higher than the maximum allowed value, it is reduced to the maximum value in step 280, an alarm is generated, and then control transfers to loop F.

Up to the beginning of loop F at step 282, the focus of control is on automatic control of $F_{IO2}$. As shown, two different mechanisms are incorporated in the control process of $F_{IO2}$ in a preferred practice of the invention. One, a rapid stepwise control scheme which responds instantly to fast declines in $S_{pO2}$, and the other, a more finely controlled PID algorithm that provides fine control of $F_{IO2}$ in the absence of sharp and hazardous declines in $S_{pO2}$. The stepwise controller in a preferred practice of the invention has three loops, each with its defined minimum and maximum $S_{pO2}$ threshold levels. These three loops were shown respectively at B, C, and D, and the PID control loop was shown at E in the flow chart of FIG. 3. The controller switches from the PID control to the rapid stepwise algorithm only if rapid declines in $S_{pO2}$ are detected. Once in the stepwise mode, the controller continuously checks $S_{pO2}$, and if it rises, the controller reduces $F_{IO2}$ to minimize the exposure of the patient to high and toxic levels of $F_{IO2}$. The controller is designed to correct hypoxemia within seconds and to avoid hyperoxemia. As shown, the controller detects artifacts in the measurement of $S_{pO2}$, discards the artifacts, and generates alarms when appropriate. The algorithm also enables clinicians to define the desired oxygenation levels for different patients. This is done by defining an appropriate $P_{aO2}$ set point, by setting the threshold values for $S_{pO2}$, and by adjusting the correction parameter, CP, in accordance with the measured pH levels in the patient's blood as described above.

After the determination of the required $F_{IO2}$, the procedure of adjusting the PEEP value is started at F in step 282. In this step, the ratio of PEEP/$F_{IO2}$ is calculated. Then in 284, the control parameter AP, which was defined in step 208, is examined. If it is less than 1, it means that PEEP is not adjusted automatically and it is instead adjusted manually by the operator. In this case, the controller merely watches the PEEP/$F_{IO2}$ ratio and generates warning signals, if the ratio is either too low or too high. In step 286, the ratio is compared to a minimum allowed value (e.g., 0.12). If it is less than the minimum value, an alarm is generated in 288 and control passes to I (which will be described later). However, if the PEEP/$F_{IO2}$ ratio is found to be equal to or greater than the minimum value in step 286, then the next step in 290 is performed where the ratio is compared to a maximum allowed value (e.g., 0.22). If the ratio is less than or equal to the maximum value, control passes to I. Otherwise, an alarm is generated in step 292 and then control is transferred to I.

Back to step 284, if AP is not less than 1, it means that PEEP should be calculated and automatically adjusted. Therefore, the automatic PEEP adjustment control loop is started next at G at step 294. In the step 296 that follows, the PEEP/$F_{IO2}$ ratio is compared to a minimum allowed value (e.g., 0.12). If it is less than the minimum, the procedure at H is started and it is examined how long ago the last adjustment in PEEP was made. In step 300 that follows, the time parameter, TP, is compared to a defined fixed interval, T1, for example 240 seconds. If TP is less than 240 seconds, it means that the last PEEP adjustment was made less than 4 minutes ago. Then the procedure at J is started. Control passes to step 302 in which no change is made in PEEP and the time parameter, TP, is increased by a fixed amount (e.g., 0.75 seconds):

$$TP_{(new)}=TP_{(old)}+0.75$$

Thereafter, control passes to I. However, if in step 300, it is found that TP is equal to or greater than 240 seconds, it means that the last adjustment in PEEP was made at least 4 minutes ago or longer. Therefore, control passes to step 304. In this step, TP is set back to zero. Then in 306 that follows, PEEP is increased by a fixed amount (e.g., 2 cm $H_2O$):

$$PEEP_{(new)}=PEEP_{(old)}+2\text{ cm }H_2O$$

Thereafter, control passes to I.

Back to step 296, if the PEEP/$F_{IO2}$ ratio is not found to be less than the minimum allowed value, control transfers to step 308. In this step the PEEP/$F_{IO2}$ ratio is compared to a maximum allowed value (e.g., 0.22). If the ratio is not less than the maximum value, step 310 is next performed. At this point, the PEEP/$F_{IO2}$ ratio is compared to a slightly higher value than the maximum, RG, (e.g., 0.24). If it is not greater than this value, control passes to J. Otherwise; step 312 is performed in which the time parameter, TP, is compared to the fixed interval of 240 seconds. If TP is less than 240 seconds, control passes to J. Otherwise; TP is set back to zero in step 314, and PEEP is reduced by a fixed amount (e.g., 2 cm $H_2O$) in step 316:

$$PEEP_{(new)}=PEEP_{(old)}-2\text{ cm }H_2O$$

Thereafter, control passes to I. In step 318 at I, the routine is held for a fixed interval (e.g., 0.75 seconds) and then control returns to the beginning of the main loop at A'.

Back to step 308, if the PEEP/$F_{IO2}$ ratio is found to be less than the maximum allowed limit (e.g., 0.22), the step 320 is next followed. In this step $S_{pO2}$ is compared to a predefined minimum allowed value (e.g., 92%). If it is higher than or at least equal to the predefined minimum value, the PEEP level is not changed and control passes to J. However, if in 320, $S_{pO2}$ is found to be less than the predefined minimum value, then control passes to H, where it is determined whether at least 4 minutes have passed since the last PEEP adjustment, and if so, PEEP is increased by a fixed amount (e.g., 2 cm $H_2$—O) as was shown earlier.

In performing the automatic PEEP adjustments, the PEEP/$F_{IO2}$ is kept within a clinically acceptable range. As shown above, if the PEEP/$F_{IO2}$ is too low, PEEP is increased by a fixed increment (e.g., 2 cm $H_2O$). Also, if the PEEP/$F_{IO2}$ ratio is within the acceptable range and $S_{pO2}$ is low, then PEEP is increased by a fixed increment (e.g., 2 cm $H_2O$) to improve patient's oxygenation. On the other hand, if the PEEP/$F_{IO2}$ ratio increases beyond a maximum defined value, the program reduces PEEP in fixed amounts (e.g., 2 cm $H_2O$). In any case, the interval between two successive PEEP adjustments is at least equal to a fixed period (e.g., 240 seconds), to allow for the changes in PEEP to have an observable and measurable impact on the patient's oxygenation.

It should be noted that the above examples for the incremental step size for PEEP adjustment (e.g. 2 cm $H_2O$) and the minimum and maximum values for the ratio of PEEP/$F_{IO2}$, are indicated for patients receiving ventilatory treatment in a more acute clinical setting such as the intensive care or a constant care unit of a hospital. Smaller incremental adjustments (e.g. 1 cm $H_2O$) and more conservative ranges for the ratio of PEEP (or CPAP)/$F_{IO2}$ may be adopted if the invention is used to improve the breathing and oxygenation of more stable, spontaneously breathing patients.

Figure 4:
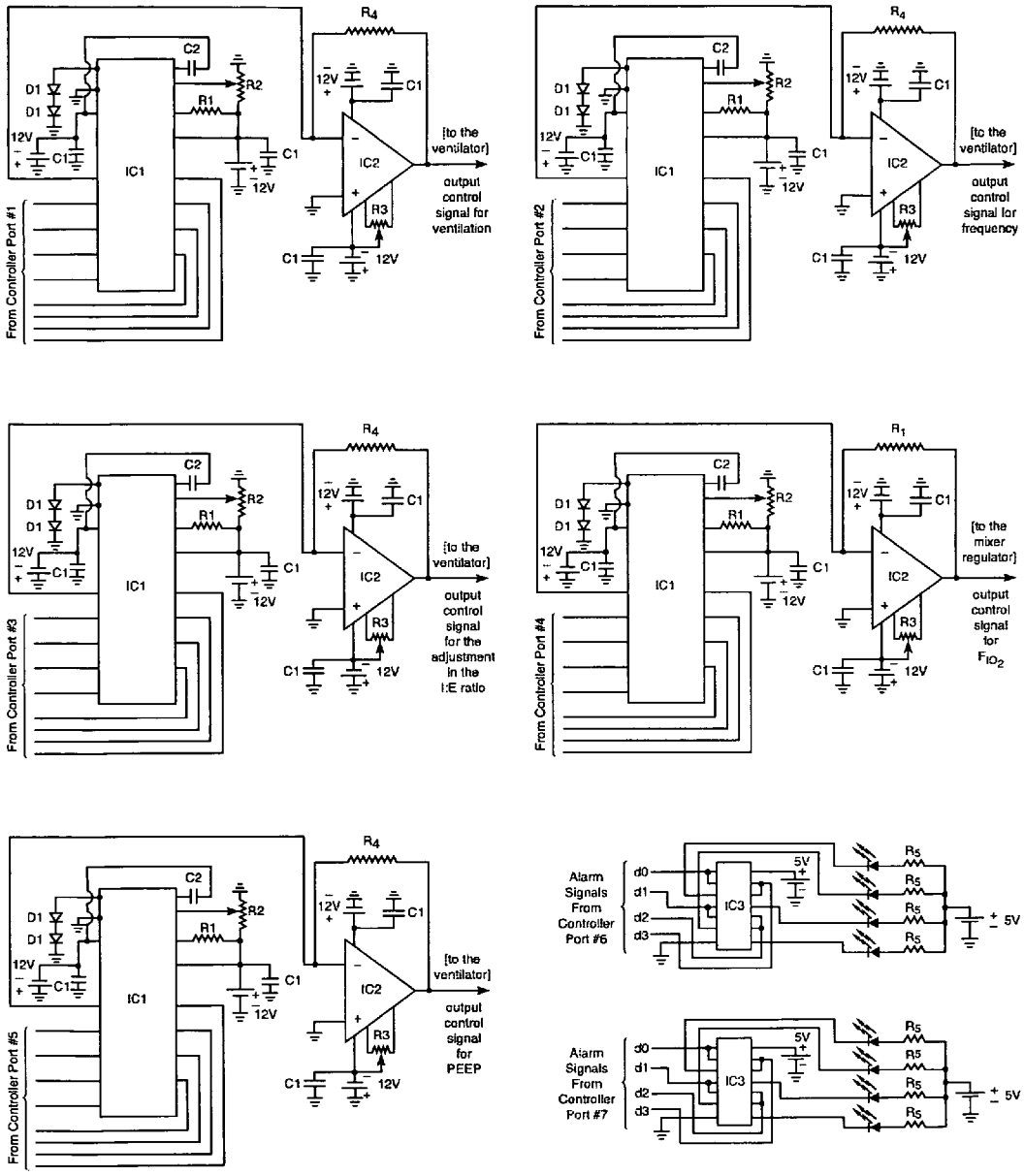

FIG. 4 illustrates in detail, a preferred circuit diagram of the Signal Generator Circuit, 46, and the alarm circuit 54. The preferred component types and values are shown in the chart below:

| Component | Type/Value |
|---|---|
| IC1 | DAC0802LCN |
| IC2 | LM741CN |
| IC3 | SN7400N |
| C1 | 0.1 μF |
| C2 | 0.03 μF |
| D1 | 1N4148 |
| $R_1$ | 5.1 kΩ |
| $R_2$ | 50 kΩ pot |
| $R_3$ | 10 kΩ pot |
| $R_4$ | 2.7 kΩ |
| $R_5$ | 330 Ω |

There has been described a method and apparatus for controlling a ventilator. The invention utilizes data indicative of measured oxygen levels of the patient to automatically control $F_{IO2}$, and PEEP (or CPAP). In an alternative embodiment, the invention further uses the respiratory mechanics data (i.e. respiratory elastance and airway resistance) to automatically make the necessary adjustments in the I:E ratio of the patient on the ventilator. It further incorporates the features of U.S. Pat. No. 4,986,268 and uses data indicative of measured levels of oxygen and the respiratory mechanics data of the patient, along with data indicative of barometric pressure (as a reference calibrating pressure), and data indicative of measured carbon dioxide level of the patient to automatically control the breathing frequency and tidal volume of breaths of the patient on the ventilator. The invention also detects and corrects artifacts in the measured oxygen and carbon dioxide data and applies safety rules. In its different embodiments, the invention can improve total and/or assist ventilatory treatments provided to different patient groups.

The present invention may be embodied in other specific forms without departing from the scope and the essential attributes thereof. Therefore, reference should be made to the appended claims rather than to the foregoing specification, with regard to the scope of the invention.

What is claimed is:

[1. An apparatus for automatically controlling a ventilator comprising:

first means for processing data indicative of at least a measured oxygen level of a patient, and for providing output data indicative of:

required concentration of oxygen in inspiratory gas of the patient ($F_{IO2}$) and positive end-expiratory pressure (PEEP) for a next breath of the patient;

wherein $F_{IO2}$ is determined to reduce the difference between the measured oxygen level of the patient and a desired value;

wherein PEEP is determined to keep a ratio of PEEP/$F_{IO2}$ within a prescribed range and, while keeping the ratio within the prescribed range, to keep the measured oxygen level of the patient above a predefined value; and second means, operatively coupled to the first means, for providing control signals, based on the output data provided by the first means, to the ventilator;

wherein the control signals provided to the ventilator automatically control PEEP, and $F_{IO2}$, for a next breath of the patient.]

[2. The apparatus of claim 1, wherein the first means comprises a programmable microcomputer.]

[3. The apparatus of claim 2, further comprising an alarm unit;

wherein the first means further determines whether there has been an artifact in the measured oxygen levels and replaces and/or corrects the data determined to be based on the artifact; and wherein the second means further provides an alarm control signal to the alarm unit to warn of the artifact in the measured oxygen levels.]

[4. The apparatus of claim 2, further comprising an alarm unit;

wherein the first means further determines whether the measured oxygen levels are outside a prescribed range; and wherein the second means further provides an alarm control signal to the alarm unit to warn of the measured oxygen level of the patient being outside a prescribed range.]

[5. The apparatus of claim 2, further comprising an analog to digital (A/D) converter connected to an input of the first means for converting analog signals from an oxygen sensor, indicative of the oxygen level of the patient, to digital data.]

[6. The apparatus of claim 5, wherein the oxygen sensor is a pulse oximeter measuring arterial hemoglobin oxygen saturation in the patient's blood.]

[7. The apparatus of claim 2, wherein data indicative of the lower inflection pressure point on an inspiratory or expiratory pressure volume curve of the patient (LIP) is provided to the first means.]

[8. The apparatus of claim 7, wherein the data indicative of LIP is supplied by a monitor operatively coupled to the first means.]

[9. The apparatus of claim 2, wherein data indicative of the patient's measured intrinsic positive end-expiratory pressure (PEEPi) is provided to the first means.]

[10. The apparatus of claim 9, wherein the data indicative of PEEPi is supplied by a monitor operatively coupled to the first means.]

[11. The apparatus of claim 2, wherein the programmable microcomputer further comprises a program means for determining from the input data: the patient's arterial partial pressure of oxygen; the required $F_{IO2}$; the required PEEP; for a next breath of the patient.]

[12. The apparatus of claim 11, wherein the program means further determines, from the input data: whether there has been an artifact in the data indicative of the measured oxygen level of the patient, and wherein the program means further replaces and/or corrects the data based on the artifact and generates a warning signal in the event the artifact is determined.]

[13. The apparatus of claim 2, wherein data corresponding to a set point for arterial partial pressure of oxygen, threshold values for the oxygen level of the patient, and a correction factor for oxygen based on measured blood pH levels of the patient are entered manually and stored in a software program.]

[14. The apparatus of claim 2, wherein the first means further processes input data indicative of respiratory elastance, respiratory airway resistance, barometric pressure, and measured carbon dioxide levels of the patient, and based upon the input data, provides digital output data indicative of required ventilation, optimum breathing frequency, and required adjustment in the ratio of inspiration time to expiration time (I:E) for a next breath of the patient, and; wherein the second means further generates additional control signals to the ventilator based on the output data of the first means; wherein the additional control signals to the ventilator control tidal volume and frequency of inhaled gas provided to the patient by the ventilator and effect necessary adjustments in the ratio of I:E for a next breath of the patient.]

[15. The apparatus of claim 14, wherein the input data indicative of respiratory elastance and airway resistance of the patient are supplied to the first means by one or more monitors coupled to the first means.]

[16. The apparatus of claim 14, wherein the input data indicative of respiratory elastance and airway resistance of the patient are entered manually and stored in a software program.]

[17. The apparatus of claim 14, wherein the input data indicative of the measured oxygen level of the patient and the measured carbon dioxide level of the patient are provided to the first means by one or more monitors coupled to the first means.]

[18. The apparatus of claim 17, wherein the input data indicative of the measured oxygen level of the patient is provided by a pulse oximeter measuring arterial hemoglobin oxygen saturation of the patient, and the input data indicative of the measured carbon dioxide level of the patient is provided by an exhaled gas analyzer detecting end-tidal partial pressure of carbon dioxide or end-tidal concentration of carbon dioxide in exhaled gas of the patient.]

[19. The apparatus of claim 17, wherein, based on data indicative of measured oxygen and carbon dioxide levels of the patient, the first means detects an artifact in the data, discards the data having the artifact, resumes a previous value of the data in a memory, and provides a warning instruction signal; and wherein the second means generates a warning control signal that is supplied to an alarm unit that generates an alarm signal.]

[20. The apparatus of claim 17, wherein, based on data indicative of measured carbon dioxide and oxygen levels of the patient, the first means detects a potential pulmonary embolism and produces digital output data indicative of predefined levels of ventilation and breathing frequency and a required adjustment in the I:E ratio, and provides a warning instruction signal; and wherein the second means generates a warning control signal.]

[21. The apparatus of claim 17, further comprising program means for determining from the input data: (i) partial pressures of oxygen and carbon dioxide in arterial blood of the patient; (ii) presence of artifact(s) in the data indicative of the measured oxygen and carbon dioxide levels of the patient, and in case of artifact detection, replacing and/or correcting the data and corresponding partial pressure value(s); (iii) net effects of oxygen and carbon dioxide on alveolar ventilation; (iv) total required alveolar ventilation; (v) optimal frequency of breathing; (vi) required ventilation; (vii) required adjustment in the I:E ratio; (viii) required $F_{IO2}$; and (ix) required PEEP; for a next breath of the patient.]

[22. The apparatus of claim 21, wherein data corresponding to a set point for arterial partial pressure of oxygen, an adjustment factor for carbon dioxide level of the patient, threshold levels for oxygen level of the patient, and a correction factor for oxygen based on measured blood pH levels of the patient, are entered manually and stored in a software program.]

[23. The apparatus of claim 14, wherein the input data indicative of barometric pressure is supplied to the first means by one or more monitors coupled to the first means.]

[24. The apparatus of claim 14, wherein the input data indicative of barometric pressure is entered manually and stored in hardware.]

[25. The apparatus of claim 14, wherein the input data indicative of barometric pressure is entered manually and stored in a software program.]

[26. The apparatus of claim 14, wherein the first means also receives and processes data indicative of the patient's metabolic rate ratio.]

[27. The apparatus of claim 26, wherein the data indicative of the patient's metabolic rate ratio is supplied to the first means by a monitor coupled to the first means.]

[28. The apparatus of claim 26, wherein the data indicative of the patient's metabolic rate ratio is entered manually and stored in a software program.]

[29. A method for automatically controlling a ventilator comprising the steps of:

(a) measuring an oxygen level of a patient and providing a data signal indicative of the measured oxygen level;

(b) determining: (i) required concentration of oxygen in an inspiratory gas of the patient, $F_{IO2}$, based on the data signal indicative of the measured oxygen level of the patient and to reduce the difference between the measured oxygen level of the patient and a desired value; (ii) required positive end-expiratory pressure, PEEP, wherein a ratio of PEEP/$F_{IO2}$ is maintained within a prescribed range, and to keep the measured oxygen level of the patient above a predefined value; and (c) providing data signals indicative of the required $F_{IO2}$ and the required PEEP based upon the determining of step (b), for automatically controlling $F_{IO2}$ and PEEP for a next breath of the patient.]

[30. The method of claim 29, wherein step (b) further comprises determining, from the data indicative of the measured oxygen level in (a), whether there has been an artifact in the measured oxygen level, and replacing and/or correcting the data signal in (a) in the event the artifact is determined.]

[31. The method of claim 29, wherein the data signal indicative of measured oxygen level of the patient is in analog form and is converted to digital form before the determining of step (b), and wherein the providing of step (c) further comprises converting the data signals from digital to analog form.]

[32. The method of claim 31, wherein the measuring of the oxygen level of the patient comprises measuring an arterial hemoglobin oxygen saturation of the patient via pulse oximetry.]

[33. The method of claim 32, wherein an arterial partial pressure of oxygen of the patient is derived from the arterial hemoglobin oxygen saturation of the patient measured by the pulse oximeter.]

[34. The method of claim 33, wherein the following equation is used to calculate the arterial partial pressure of oxygen ($P_{aO2}$) of the patient from the arterial hemoglobin oxygen saturation data ($S_{pO2}$) measured by pulse oximetry:

$$P_{aO_2} = \frac{-\ln\left[1-\left(S_{pO_2}\right)^{0.5}\right]}{0.046} + CP$$

where $P_{aO2}$ is in mm Hg and CP is a correction parameter which is used to shift $P_{aO2}$ and CP is based on the patient's measured blood pH level.]

[35. The method of claim 34, further comprising:

comparing $P_{aO2}$ to a minimum acceptable value, and, if $P_{aO2}$ is found to be less than the minimum acceptable value:

discarding $P_{aO2}$ and a latest measured $S_{pO2}$ data;

resuming previous values of $P_{aO2}$ and $S_{pO2}$; and generating a warning signal.]

[36. The method of claim 29, wherein data corresponding to the lower inflection pressure point on an inspiratory or expiratory pressure volume curve of the patient (LIP) is also provided in step (a), and an initial value for PEEP is set equal to LIP plus 0 to 8 cm $H_2O$ and the initial value for PEEP is provided in step (b).]

[37. The method of claim 36, wherein the data corresponding to LIP is supplied by a monitor.]

[38. The method of claim 29, wherein data corresponding to the measured intrinsic PEEP of the patient (PEEPi) is also provided in step (a), and an initial value for PEEP is set between 80% and 100% of PEEPi and the initial value for PEEP is provided in step (b).]

[39. The method of claim 38, wherein the data corresponding to PEEPi is supplied by a monitor.]

[40. The method of claim 29, wherein an initial value for PEEP is determined by the operator and is manually provided.]

[41. The method of claim 29, wherein the required concentration of oxygen in the inspiratory gas of the patient ($F_{IO2}$) is calculated by using a stepwise control scheme and/or by using a proportional-integral-derivative (PID) technique.]

[42. The method of claim 41, wherein using a PID technique comprises comparing $S_{pO2}$ obtained by pulse oximetry to a defined minimum safe value, and wherein using the PID technique continues while $S_{pO2}$ is greater than the defined minimum safe value.]

[43. The method of claim 41, wherein using a PID technique comprises comparing $S_{pO2}$ obtained by pulse oximetry to a defined minimum safe value, and wherein, if $S_{pO2}$ is found to be less than or equal to the defined minimum safe value, a stepwise control scheme is followed that comprises the steps of:

raising $F_{IO2}$ stepwise to avoid hypoxemia, allowing $F_{IO2}$ to remain high until $S_{pO2}$ rises to a second threshold value, lowering $F_{IO2}$ stepwise, comparing $S_{pO2}$ to a third threshold value, lowering $F_{IO2}$ stepwise upon $S_{pO2}$ rising to the third threshold value, comparing $S_{pO2}$ to a fourth threshold value, returning control to the PID technique upon $S_{pO2}$ rising to the fourth threshold value.]

[44. The method of claim 41, wherein the difference between a $P_{aO2}$ set point and the $P_{aO2}$ of the patient is reduced by using a PID control procedure according to the following equations:

$$Y_1(k)=P_{aO2}(\text{set-point})-P_{aO2}$$

$$Y_2(k)=[Y_1(k)-Y_1(k-1)]/T$$

$$Y_3(k)=Y_3(k-1)+TY_1(k)$$

$$E(k)=\alpha Y_1(k)+\beta Y_3(k)+\gamma Y_2(k)$$

$$G(k)=E(k)+0.21$$

where $Y_1(k)$, $Y_2(k)$, and $Y_3(k)$ are the proportional, derivative, and integral components of error, respectively, E(k) is an error function, T is a sampling interval, G(k) is the required $F_{IO2}$, and parameters $\alpha$, $\beta$, and $\gamma$ are PID coefficients.]

[45. The method of claim 41, wherein the determining of required PEEP of the patient comprises the following procedure:

comparing the PEEP/$F_{IO2}$ ratio to a defined minimum allowed value, increasing PEEP by a fixed incremental value if the PEEP/$F_{IO2}$ ratio is lower than the defined minimum allowed value and the time elapsed since the last adjustment in PEEP is longer than or equal to a fixed defined interval T1, comparing the PEEP/$F_{IO2}$ ratio with a defined maximum allowed value if the PEEP/$F_{IO2}$ ratio is not less than the defined minimum allowed value, comparing $S_{pO2}$ with a defined value if the PEEP/$F_{IO2}$ ratio is less than the defined maximum allowed value, increasing PEEP by a fixed incremental value if $S_{pO2}$ is less than the defined value and the time elapsed since the last adjustment in PEEP is longer than or equal to T1, if the PEEP/$F_{IO2}$ ratio is not less than the defined maximum allowed value, comparing the PEEP/$F_{IO2}$ ratio to a value higher than the defined maximum allowed value, RG, whereby if the PEEP/$F_{IO2}$ ratio is higher than RG, and the time elapsed since the last adjustment in PEEP is greater than or equal to T1, decreasing PEEP by a fixed incremental amount.]

*46. An apparatus for automatically controlling a ventilator for a next breath of a patient comprising:*

*first means for processing input data indicative of at least a measured oxygen level of the patient, and for providing output data indicative of:*

*required concentration of oxygen in inspiratory gas of the patient ($F_{IO2}$) and required positive end-expiratory pressure (PEEP) for a next breath of the patient,*

*wherein $F_{IO2}$ is determined to reduce the difference between the measured oxygen level of the patient and a desired value;*

*wherein a ratio of PEEP/$F_{IO2}$ is calculated and PEEP is determined to keep said ratio of PEEP/$F_{IO2}$ within one prescribed range;*

*wherein PEEP is determined without using a proportional-integral-derivative (PID) control procedure and while PEEP is determined to keep the ratio of PEEP/$F_{IO2}$ within one prescribed range, PEEP is determined to also keep the measured oxygen level of the patient above a predefined value; and*

*second means, operatively coupled to the first means, for providing control signals, based on the output data provided by the first means, to the ventilator for PEEP and to a mixer regulator, operatively coupled to the ventilator, for $F_{IO2}$;*

*wherein the control signals automatically control PEEP and $F_{IO2}$ for a next breath of the patient.*

*47. The apparatus of claim 46, wherein the first means comprises a programmable microcomputer.*

*48. The apparatus of claim 47, further comprising an alarm unit;*

*wherein the first means further determines whether there has been an artifact in the measured oxygen level and in response to determining an artifact is present, replaces the measured oxygen level with the artifact with a most recent measured oxygen level without artifact; and*

*wherein the second means further provides an alarm control signal to the alarm unit in response to the determination by the first means that there has been an artifact to warn of an artifact in the current measured oxygen level.*

*49. The apparatus of claim 47, further comprising an alarm unit;*

*wherein the first means further determines whether the measured oxygen level is outside a prescribed range; and*

*wherein the second means further provides an alarm control signal to the alarm unit in response to the determination by the first means that the measured oxygen level is outside the prescribed range to warn of the measured oxygen level of the patient being outside the prescribed range.*

*50. The apparatus of claim 47, wherein the input data indicative of at least the measured oxygen level of the patient processed by the first means includes arterial hemoglobin oxygen saturation data measured by a pulse oximeter operatively coupled to the first means.*

*51. The apparatus of claim 47, wherein data indicative of a lower inflection pressure point on an inspiratory or expiratory pressure volume curve of the patient (LIP) is provided to the first means.*

*52. The apparatus of claim 51, wherein the data indicative of LIP is supplied by a monitor operatively coupled to the first means.*

*53. The apparatus of claim 47, wherein data indicative of the patient's measured intrinsic positive end-expiratory pressure (PEEPi) is provided to the first means.*

*54. The apparatus of claim 53, wherein the data indicative of PEEPi is supplied by a monitor operatively coupled to the first means.*

*55. The apparatus of claim 47, wherein the programmable microcomputer further comprises a program means for determining from the input data:*

*a patient's arterial partial pressure of oxygen;*

*the required $F_{IO2}$; and*

*the required PEEP*

*for a next breath of the patient.*

*56. The apparatus of claim 55, wherein the program means further determines, from the input data:*

*whether there has been an artifact in the measured oxygen level of the patient, and*

*wherein the program means, in response to determining an artifact is present, further replaces the measured oxygen level with the artifact with a most recent measured oxygen level without artifact, and*

*the apparatus further comprising alarm means for generating a warning signal in the event the artifact is determined to be present.*

*57. The apparatus of claim 47, wherein data corresponding to a set point for arterial partial pressure of oxygen, threshold values for arterial hemoglobin oxygen saturation level of the patient, and a correction factor for arterial partial pressure of oxygen based on measured blood pH levels of the patient are entered manually and stored in a software program.*

*58. The apparatus of claim 47, wherein input data indicative of at least a measured oxygen level of the patient which is processed by the first means further includes input data indicative of respiratory elastance, respiratory airway resistance, barometric pressure, and measured carbon dioxide level of the patient, and based upon the input data, the first means provides digital output data indicative of required ventilation, optimum breathing frequency, and required adjustment in the ratio of inspiration time to expiration time (I:E) for a next breath of the patient;*

*wherein the second means further generates additional control signals to the ventilator based on the digital output data of the first means; and*

*wherein the additional control signals to the ventilator control tidal volume and frequency of inhaled gas provided to the patient by the ventilator and effect necessary adjustments in the ratio of I:E for a next breath of the patient.*

*59. The apparatus of claim 58, wherein the input data indicative of respiratory elastance and airway resistance of the patient are supplied to the first means by one or more monitors coupled to the first means.*

*60. The apparatus of claim 58, wherein the input data indicative of respiratory elastance and airway resistance of the patient are entered manually and stored in a software program.*

*61. The apparatus of claim 58, wherein the input data indicative of the measured oxygen level of the patient and the measured carbon dioxide level of the patient are provided to the first means by one or more monitors coupled to the first means.*

*62. The apparatus of claim 61, wherein the input data indicative of the measured oxygen level of the patient is provided by a pulse oximeter measuring arterial hemoglobin oxygen saturation of the patient, and the input data indicative of the measured carbon dioxide level of the patient is provided by an exhaled gas analyzer detecting end-tidal partial pressure of carbon dioxide or end-tidal concentration of carbon dioxide in exhaled gas of the patient.*

*63. The apparatus of claim 61, wherein, based on the input data indicative of the measured oxygen level and the measured carbon dioxide level of the patient, the first means detects an artifact in the input data indicative of the measured oxygen level and/or the measured carbon dioxide level of the patient, discards the input data indicative of the measured oxygen level and/or the measured carbon dioxide level of the patient having the artifact, and resumes a value of data indicative of the most recent measured oxygen level without artifact and/or the most recent measured carbon dioxide level without artifact stored in a memory; and wherein the second means generates a warning control signal that is supplied to an alarm unit that generates an alarm signal.*

*64. The apparatus of claim 61, wherein, based on the input data indicative of the measured carbon dioxide level and the measured oxygen level of the patient, the first means detects a potential pulmonary embolism and produces digital output data indicative of predefined levels of ventilation and breathing frequency and a required adjustment in the I:E ratio, and provides a warning instruction signal; and wherein the second means generates a warning control signal in response to the warning instruction signal provided by the first means.*

*65. The apparatus of claim 61, wherein the first means comprises a first control program means for determining from the input data:*

*(i) partial pressures of oxygen and carbon dioxide in arterial blood of the patient;*

*(ii) presence of artifact(s) in the input data indicative of the measured oxygen level and/or carbon dioxide level of the patient, and in case of artifact detection, replacing the input data indicative of the measured oxygen level and/or carbon dioxide level of the patient with the artifact and corresponding partial pressure value with data indicative of most recent measured oxygen level without an artifact and/or the measured carbon dioxide level without artifact and corresponding partial pressure value(s);*

*(iii) net effects of oxygen and carbon dioxide on alveolar ventilation;*

*(iv) total required alveolar ventilation;*

*(v) the optimal frequency of breathing;*

*(vi) the required ventilation; and*

*(vii) the required adjustment in the I:E ratio*

*for a next breath of the patient; and*

*a second control program means for determining:*

*(i) the required $F_{IO2}$; and*

*(ii) the required PEEP*

*for a next breath of the patient.*

*66. The apparatus of claim 65, wherein data corresponding to a set point for the arterial partial pressure of oxygen, an adjustment factor for the measured carbon dioxide level of the patient, threshold levels for arterial hemoglobin oxygen saturation level of the patient, and a correction factor for the arterial partial pressure of oxygen based on measured blood pH levels of the patient are entered manually and stored in a software program.*

*67. The apparatus of claim 58, wherein the input data indicative of barometric pressure is supplied to the first means by one or more monitors coupled to the first means.*

*68. The apparatus of claim 58, wherein the input data indicative of barometric pressure is entered manually and stored in hardware.*

*69. The apparatus of claim 58, wherein the input data indicative of barometric pressure is entered manually and stored in a software program.*

*70. The apparatus of claim 58, wherein the first means also receives and processes data indicative of the patient's metabolic rate ratio.*

71. The apparatus of claim 70, wherein the data indicative of the patient's metabolic rate ratio is entered manually and stored in a software program.

72. A method for automatically controlling a ventilator for a next breath of a patient comprising the steps of:

(a) measuring an oxygen level of the patient and providing a data signal indicative of the measured oxygen level;

(b) determining for a next breath of the patient:

(i) required concentration of oxygen in an inspiratory gas of the patient, $F_{IO2}$, based on the data signal indicative of the measured oxygen level of the patient, to reduce the difference between the measured oxygen level of the patient and a desired value; and (ii) required positive end expiratory pressure, PEEP, wherein a ratio of PEEP/$F_{IO2}$ is calculated and PEEP is determined to keep said ratio of PEEP/$F_{IO2}$ within one prescribed range, wherein PEEP is determined without using a proportional-integral-derivative (PID) control procedure, and while PEEP is determined to keep the ratio of PEEP/$F_{IO2}$ within one prescribed range, PEEP is determined to also keep the measured oxygen level of the patient above a predefined value; and (c) providing data signals indicative of the required $F_{IO2}$ and the required PEEP, based upon the determining of step (b), for automatically controlling $F_{IO2}$ and PEEP for a next breath of the patient.

73. The method of claim 72, wherein step (b) further comprises determining, from the data signal indicative of the measured oxygen level in step (a), whether there has been an artifact in the measured oxygen level, and, in the event an artifact is determined, replacing the measured oxygen level with the artifact with a most recent measured oxygen level without artifact.

74. The method of claim 72, wherein the measuring of the oxygen level of the patient comprises measuring an arterial hemoglobin oxygen saturation of the patient via pulse oximetry.

75. The method of claim 74, wherein an arterial partial pressure of oxygen of the patient is derived from the arterial hemoglobin oxygen saturation of the patient ($S_{pO2}$) measured by a pulse oximeter.

76. The method of claim 75, wherein the following equation is used to calculate the arterial partial pressure of oxygen ($P_{aO2}$) of the patient from the arterial hemoglobin oxygen saturation data ($S_{pO2}$) measured by pulse oximetry:

$$P_{aO_2} = \frac{-\ln\left[1-\left(S_{pO_2}\right)^{0.5}\right]}{0.046} + CP$$

where $P_{aO2}$ is in mm Hg and CP is a correction parameter which is used to shift $P_{aO2}$ and CP is based on a measured blood pH level of the patient.

77. The method of claim 76, further comprising: comparing $P_{aO2}$ to a minimum acceptable value, and, if $P_{aO2}$ is found to be less than the minimum acceptable value, discarding the $P_{aO2}$ found to be less than the minimum acceptable value and a latest measured $S_{pO2}$ data corresponding thereto; resuming a most recent value of $P_{aO2}$ found to be equal to or greater than the minimum acceptable value and corresponding value of $S_{pO2}$; and generating, by a signal generator, a warning signal.

78. The method of claim 72, wherein data corresponding to the lower inflection pressure point on an inspiratory or expiratory pressure volume curve of the patient (LIP) is also provided in step (a), and an initial value for PEEP is set equal to LIP plus 0 to 8 cm $H_2O$ and the initial value for PEEP is provided in step (b).

79. The method of claim 78, wherein the data corresponding to LIP is supplied by a monitor.

80. The method of claim 72, wherein data corresponding to a measured intrinsic PEEP of the patient (PEEPi) is also provided in step (a), and an initial value for PEEP is set between 80% and 85% of PEEPi and the initial value for PEEP is provided in step (b).

81. The method of claim 80, wherein the data corresponding to PEEPi is supplied by a monitor.

82. The method of claim 72, wherein an initial value for PEEP is determined by the operator and is manually provided.

83. The method of claim 72, wherein the required concentration of oxygen in the inspiratory gas of the patient ($F_{IO2}$) in step (b)(i) is calculated by using a stepwise control scheme and/or by using a proportional-integral-derivative (PID) control procedure.

84. The method of claim 83, wherein using the PID control procedure comprises comparing $S_{pO2}$ obtained by pulse oximetry to a defined minimum safe value, and wherein using the PID control procedure continues while $S_{pO2}$ is greater than the defined minimum safe value.

85. The method of claim 83, wherein using the PID control procedure comprises comparing $S_{pO2}$ obtained by pulse oximetry to a defined minimum safe value, and wherein, if $S_{pO2}$ is found to be less than or equal to the defined minimum safe value, the stepwise control scheme is followed and comprises the steps of:

raising $F_{IO2}$ stepwise to avoid hypoxemia, allowing $F_{IO2}$ to remain high until $S_{pO2}$ rises to a second threshold value, lowering $F_{IO2}$ stepwise, comparing $S_{pO2}$ to a third threshold value, lowering $F_{IO2}$ stepwise upon $S_{pO2}$ rising to the third threshold value, comparing $S_{pO2}$ to a fourth threshold value, returning control to the PID control procedure upon $S_{pO2}$ rising to the fourth threshold value.

86. The method of claim 83, wherein the difference between a $P_{aO2}$ set point and a $P_{aO2}$ of the patient is reduced by using the PID control procedure according to the following equations:

$$Y_1(K)=P_{aO2}\,(set\text{-}point)-P_{aO2}$$

$$Y_2(K)=[Y_1(K)-Y_1(K-1)]/T$$

$$Y_3(K)=Y_3(K-1)+TY_1(K)$$

$$E(K)=\alpha Y_1(K)+\beta Y_3(K)+\gamma Y_2(K)$$

$$G(K)=E(K)+0.21$$

where $Y_1(k)$, $Y_2(k)$, and $Y_3(k)$ are the proportional, derivative, and integral components of error, respectively, $E(k)$ is an error function, $T$ is a sampling interval, $G(k)$ is the required $F_{IO2}$, and parameters $\alpha$, $\beta$, and $\gamma$ are PID coefficients.

87. The method of claim 83, wherein the determining of required PEEP of the patient comprises the following procedure:

comparing the PEEP/$F_{IO2}$ ratio to a defined minimum allowed value, increasing PEEP by a fixed incremental value if the PEEP/$F_{IO2}$ ratio is lower than the defined minimum

*allowed value and a time elapsed since the last adjustment in PEEP is longer than or equal to a fixed defined interval T1,*

*comparing the PEEP/$F_{IO2}$ ratio with a defined maximum allowed value if the PEEP/$F_{IO2}$ ratio is not less than the defined minimum allowed value,*

*comparing $S_{pO2}$ with a defined value if the PEEP/$F_{IO2}$ ratio is less than the defined maximum allowed value,*

*increasing PEEP by a fixed incremental value if $S_{pO2}$ is less than the defined value and the time elapsed since the last adjustment in PEEP is longer than or equal to T1, if the PEEP/$F_{IO2}$ ratio is not less than the defined maximum allowed value, comparing the PEEP/$F_{IO2}$ ratio to a value higher than the defined maximum allowed value, RG, whereby if the PEEP/$F_{IO2}$ ratio is higher than RG, and the time elapsed since the last adjustment in PEEP is greater than or equal to T1, decreasing PEEP by a fixed incremental amount.*

* * * * *